(12) United States Patent
Ortac et al.

(10) Patent No.: US 9,089,498 B2
(45) Date of Patent: Jul. 28, 2015

(54) MULTIFUNCTIONAL NANOPARTICLE DESIGNS AND APPLICATIONS

(75) Inventors: Inanc Ortac, La Jolla, CA (US); Sadik C. Esener, Solana Beach, CA (US); Jian Yang, Kingston (CA); William Trogler, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/111,713

(22) PCT Filed: Apr. 16, 2012

(86) PCT No.: PCT/US2012/033853
§ 371 (c)(1),
(2), (4) Date: Jan. 28, 2014

(87) PCT Pub. No.: WO2012/142625
PCT Pub. Date: Oct. 18, 2012

(65) Prior Publication Data
US 2014/0127305 A1 May 8, 2014

Related U.S. Application Data

(60) Provisional application No. 61/475,649, filed on Apr. 14, 2011.

(51) Int. Cl.
*A61K 9/50* (2006.01)
*B29C 67/20* (2006.01)
*B01J 20/28* (2006.01)
(Continued)

(52) U.S. Cl.
CPC ............. *A61K 9/5073* (2013.01); *A61K 9/5115* (2013.01); *A61K 9/5146* (2013.01); *A61K 9/5192* (2013.01); *B01J 13/22* (2013.01); *B01J 20/28021* (2013.01); *B29C 67/202* (2013.01);
(Continued)

(58) Field of Classification Search
CPC ......................... Y10S 977/773; Y10S 977/906
See application file for complete search history.

(56) References Cited

U.S. PATENT DOCUMENTS 6,479,146 B1  11/2002  Caruso et al.
7,045,146 B2   5/2006  Caruso et al.
(Continued)

FOREIGN PATENT DOCUMENTS

WO    WO 2009023697 A2 *  2/2009

OTHER PUBLICATIONS

K Cheng, S Sun. "Recent advances in syntheses and therapeutic applications of multifunctional porous hollow nanoparticles." Nano Today, vol. 5, 2010, pp. 183-196, Available Online May 1, 2010.*
(Continued)

*Primary Examiner* — Isaac Shomer
(74) *Attorney, Agent, or Firm* — Perkins Coie LLP

(57) ABSTRACT

Methods, structures, devices and systems are disclosed for fabricating and implementing nanoparticles with hollow core and sealable holes. In one aspect, a nanoparticle device can includes a shell structure including at least two layers including an internal layer and an external layer, the internal layer structured to enclose a hollow interior region and include one or more holes penetrating the internal layer, the external layer is of a porous material and formed around the internal layer and sealing the one or more holes, and a substance contained within the hollow interior region, the substance incapable of passing through the external layer.

18 Claims, 18 Drawing Sheets

(51) Int. Cl.
  *B01J 13/22* (2006.01)
  *B82B 3/00* (2006.01)
  *A61K 9/51* (2006.01)

(52) U.S. Cl.
  CPC ............ *B29C 67/205* (2013.01); *B82B 3/0019* (2013.01); *Y10T 428/2989* (2015.01)

(56) References Cited

U.S. PATENT DOCUMENTS

| | | |
|---|---|---|
| 2005/0244322 A1 | 11/2005 | Chen et al. |
| 2007/0111002 A1 | 5/2007 | Xia et al. |
| 2008/0311182 A1* | 12/2008 | Ferrari et al. .................. 424/450 |

OTHER PUBLICATIONS

K Cheng, S Sun. "Recent Advances in Syntheses and Therapeutic Applications of Multifunctional Porous Hollow Nanoparticles." Nano Today, vol. 5, 2010, pp. 183-196.*

G Xu, HL McLeod. "Strategies for Enzyme/Prodrug Cancer Therapy." Clinical Cancer Research, vol. 7, Nov. 2001, pp. 3314-3324.*

D Kim. "pH-Sensitive Micelle for Multidrug Resistant Tumors." PhD Thesis, University of Utah. Dec. 2009, pages include a title page, pp. i-xxi and 1-207.*

M Roberts, M Reiss, G Monger. " Advanced Biology." Cheltenham, UK, Nelson Publishers, 2000, ISBN: 0-17-438732-6, 803 pages. Title page, copyright page, and p. 45 are included.*

Huennekens, "Tumor targeting: activation of prodrugs by enzyme-monoclonal antibody conjugates", Tibtech, vol. 12, Jun. 1994, pp. 234-239.

Duziubla et al., "Polymer nanocarriers protecting active enzyme cargo against proteolysis", Journal of Controlled Release 102, 2005, pp. 427-439.

Johansson, et al., "IdeS: A Bacterial Proteolytic Enzyme with Therapeutic Potential", PLoS ONE, vol. 3, Issue 2, Feb. 2008, 6 pages.

Napierska et al., "The nanosilica hazard: another variable entity", Particle and Fibre Toxicology, 7:39, 2010, 32 pages.

Guo et al., "Facile Synthesis of Hierarchically Mesoporous Silica Particles with Controllable Cavity in Their Surfaces", Langmuir, 26(2), 2010, pp. 702-708.

Popplewell et al., "Kinetics of uptake and elimination of silicic acid by a human subject: A novel application of 32Si and accelerator mass spectrometry", J. Inorg. Biochem., 69, 1998, pp. 177-180.

Radin et al., "In vitro bioactivity and degradation behavior of silica xerogels intended as controlled release materials", Biomaterials 23, 2002, pp. 3113-3122,.

Radin et al., "In vivo tissue response to resorbable silica xerogels as controlled-release materials" Biomaterials 26, 2005, pp. 1043-1052.

Caruso et al., "Hollow Titania Spheres from Layered Precursor Deposition on Sacrificial Colloidal Core Particles", Adv. Mater., 13, No. 10, May 17, 2001, pp. 740-744.

Caruso et al., "Nanoengineering of Inorganic and Hybrid Hollow Spheres by Colloidal Templating", Science, vol. 282, Nov. 6, 1998, pp. 1111-1115.

MacDonald et al., "Hybrid nanoscale inorganic cages", Nature Materials, vol. 9, Oct. 2010, pp. 810-815.

Dinsmore et al. Colloidosomes: Selectively Permeable Capsules Composed of Colloidal Particles. (2002).at http://citeseerx.ist.psu.edu/viewdoc/summary?doi=10.1.1.7.166, 4 pages.

Arnal et al., "High-Temperature—Stable Catalysts by Hollow Sphere Encapsulation", Angewandte Chemie 118, 2006, pp. 8404-8407.

Rapoport et al., "Hollow nanoparticles of WS2 as potential solid-state lubricants", Nature 387, 1997, pp. 791-793.

Skrabalak et al., "Facile synthesis of Ag nanocubes and Au nanocages", Nat. Protocols 2, 2007, pp. 2182-2190.

Im et al., "Polymer hollow particles with controllable holes in their surfaces", Nat Mater 4, 2005, pp. 671-675.

Blanco et al., "Large-scale synthesis of a silicon photonic crystal with a complete three-dimensional bandgap near 1.5 micrometres", Nature 405, 2000, pp. 437-440.

Cochran, Ceramic hollow spheres and their applications. Current Opinion in Solid State and Materials Science 3, 1998, pp. 474-479.

Kim et al., Fabrication of Hollow Palladium Spheres and Their Successful Application to the Recyclable Heterogeneous Catalyst for Suzuki Coupling Reactions. J. Am. Chem. Soc. 124, 2002, pp. 7642-7643.

Fujiwara et al., "Direct encapsulation of BSA and DNA into silica microcapsules (hollow spheres)", J Biomed Mater Res A 81, 2007, pp. 103-112.

Zhao et al., "Fabrication of silica nanoparticles and hollow spheres using ionic liquid microemulsion droplets as templates", Colloids and Surfaces A: Physicochemical and Engineering Aspects 346, 2009, pp. 229-236.

Liu et al., From Hollow Nanosphere to Hollow Microsphere: Mild Buffer Provides Easy Access to Tunable Silica Structure. J. Phys. Chem. C 112, 2008, pp. 16445-16451.

Pan et al., "A novel synthesis of micrometer silica hollow sphere", Materials Research Bulletin 44, 2009, pp. 280-283.

Hentze et al., "Silica Hollow Spheres by Templating of Catanionic Vesicles", Society 19, 2003, pp. 1069-1074.

Ma et al., "Solution-phase synthesis of inorganic hollow structures by templating strategies", Journal of Colloid and Interface Science 335, 2009, pp. 1-10.

Yang et al., "Synthesis of Hollow Silica and Titania Nanospheres", Chem. Mater. 20, 2008, pp. 2875-2877.

Zhong et al., "Preparation of Mesoscale Hollow Spheres of TiO2 and SnO2 by Templating Against Crystalline Arrays of Polystyrene Beads", Advanced Materials 12, 2009, pp. 206-209.

Marinakos et al., "Gold Particles as Templates for the Synthesis of Hollow Polymer Capsules. Control of Capsule Dimensions and Guest Encapsulation", J. Am. Chem. Soc. 121, 1999, pp. 8518-8522.

Fleming et al., "Nanosphere-Microsphere Assembly: Methods for Core-Shell Materials Preparation", Chem. Mater. 13, 2001, pp. 2210-2216.

Tasciotti et al., "Mesoporous silicon particles as a multistage delivery system for imaging and therapeutic applications", Nat Nano 3, 2008, pp. 151-157.

Torney et al., "Mesoporous silica nanoparticles deliver DNA and chemicals into plants", Nat Nano 2, 2007, pp. 295-300.

Sokolov et al., "Novel Fluorescent Silica Nanoparticles: Towards Ultrabright Silica Nanoparticles", Small 4, 2008, 934-939.

Zhu et al. "Stimuli-responsive controlled drug release from a hollow mesoporous silica sphere/polyelectrolyte multilayer core-shell structure", Angew. Chem. Int. Ed. Engl. 44, 2005, pp. 5083-5087.

Yang et al., "Magnetite—Containing Spherical Silica Nanoparticles for Biocatalysis and Bioseparations", Anal. Chem. 76, 2004, 1316-1321.

Slowing et al., "Mesoporous silica nanoparticles as controlled release drug delivery and gene transfection carriers", Advanced Drug Delivery Reviews 60, 2008, pp. 1278-1288.

Xu et al., "Inorganic nanoparticles as carriers for efficient cellular delivery", Chemical Engineering Science 61, 2006, 1027-1040.

Piras et al., "A new biocompatible nanoparticle delivery system for the release of fibrinolytic drugs", Int J Pharm 357, 2008, pp. 260-271.

Reddy et al., "Nanoparticle-mediated delivery of superoxide dismutase to the brain: an effective strategy to reduce ischemia-reperfusion injury", FASEB J. 23, 2009, pp. 1384-1395.

Willer et al., "Anti-*E.coli* asparaginase antibody levels determined the activity of second line treatment with pegylated *E.coli* asparaginase: a retrospective analysis within ALL-BFM-trials", Blood, vol. 118, No. 22, Nov. 24, 2011, pp. 5774-5783.

Morris et al., "Divita, G. A peptide carrier for the delivery of biologically active proteins into mammalian cells", Nat Biotech 19, 2001, pp. 1173-1176.

Bush et al., "Updated Functional Classification of β-Lactamases", Antimicrobial Agents and Chemotherapy 54, 2010, pp. 969-976.

(56) References Cited

OTHER PUBLICATIONS

Bagshawe, "Antibody-Directed Enzyme Prodrug Therapy", Prodrugs V, 2011, pp. 525-540.
Vrudhula et al., "Cephalosporin Derivatives of Doxorubicin as Prodrugs for Activation by Monoclonal Antibody-.beta.-Lactamase Conjugates", J. Med. Chem. 38, 1995, pp. 1380-1385.
Rooseboom et al., Enzyme-Catalyzed Activation of Anticancer Prodrugs. Pharmacological Reviews 56, 2004, pp. 53-102.
Zlokarnik et al., "Quantitation of Transcription and Clonal Selection of Single Living Cells with β-Lactamase as Reporter", Science 279, 1998, pp. 84-88.
Gao et al., "Novel fluorogenic substrates for imaging 6-lactamase gene expression", J. Am. Chem. Soc. 125, 2003, pp. 11146-11147.
Park, Jong Chul, Authorized Officer, Korean Intellectual Property Office, International Search Report, PCT Application No. PCT/US2012/033853, Nov. 1, 2012, 10 pages.

\* cited by examiner

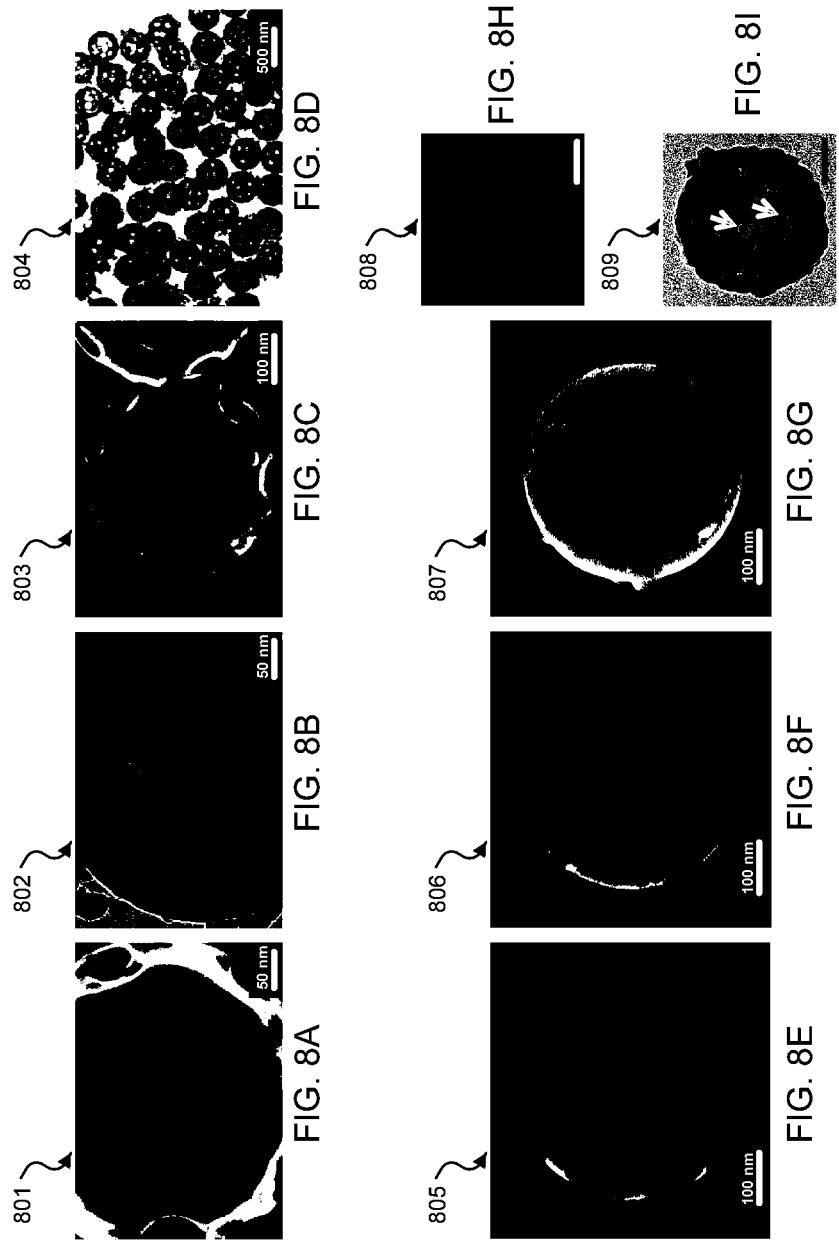

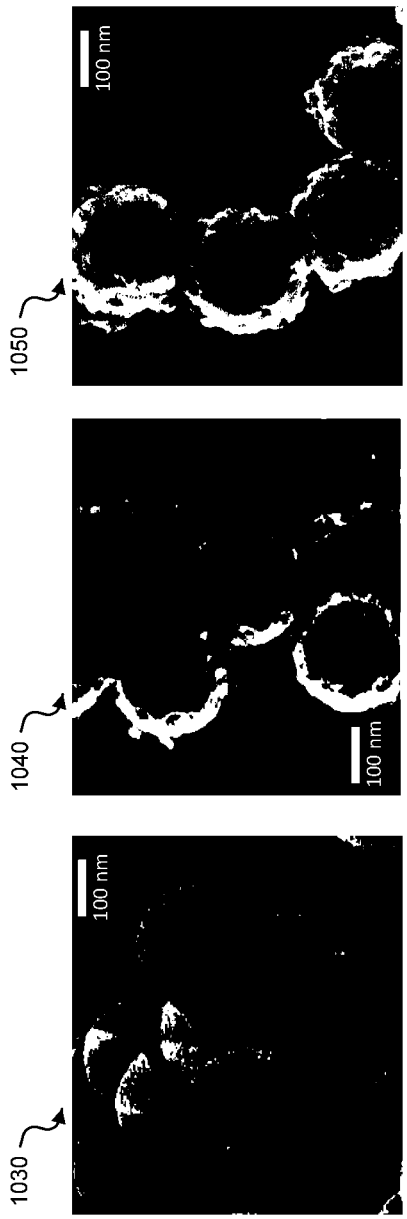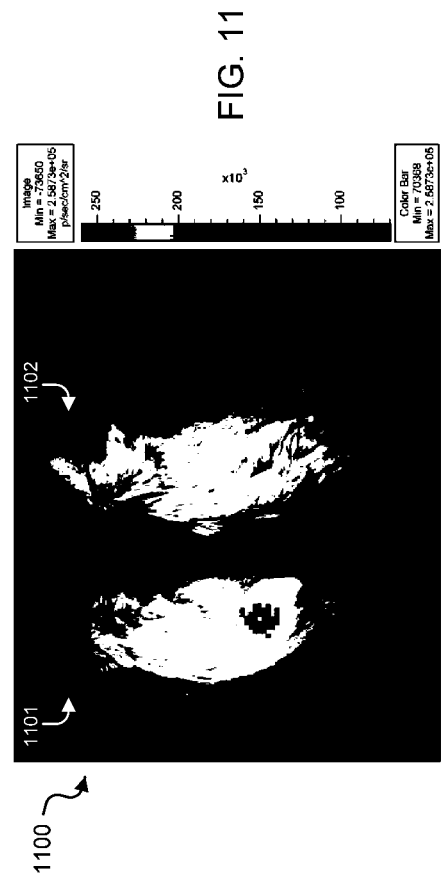

MULTIFUNCTIONAL NANOPARTICLE DESIGNS AND APPLICATIONS

CROSS REFERENCE TO RELATED APPLICATIONS

This patent document is a 35 USC § 371 National Stage application of International Application No. PCT/US2012/033853, filed on Apr. 16, 2012, which claims the priority of U.S. Provisional Application No. 61/475,649, filed on Apr. 14, 2011. The entire content of the before-mentioned patent applications is incorporated by reference as part of the disclosure of this application.

STATEMENT REGARDING FEDERALLY SPONSORED RESEARCH OR DEVELOPMENT

This invention was made with government support under grant CA119335 awarded by the National Institutes of Health. The government has certain rights in the invention.

TECHNICAL FIELD

This patent document relates to nanotechnologies.

BACKGROUND

Nanotechnology provides techniques or processes for fabricating structures, devices, and systems with features at a molecular or atomic scale, e.g., structures in a range of one to hundreds of nanometers in some applications. For example, nano-scale devices can be configured to sizes within one hundred to ten thousand times smaller than human cells, e.g., similar in size to some large biological molecules (biomolecules) such as enzymes and receptors. Nano-sized materials used to create a nanostructure, nanodevice, or a nanosystem that can exhibit various unique properties that are not present in the same materials scaled at larger dimensions and such unique properties can be exploited for a wide range of applications.

SUMMARY

Techniques, systems, and devices are described for fabricating and implementing nanostructures or nanoparticles that include a hollow core and sealable holes.

In one aspect of the disclosed technology, a method of fabricating a particle includes combining a core particle with one or more masking particles to form a template, in which the one or more masking particles bind to the core particle and cover one or more regions of the surface of the core particle, each of the one or more regions corresponding to a surface area formed between each of the one or more masking particles and the core particle, forming a layer of a porous material over the template, in which the layer forms over the surface of the core particle excluding the covered one or more regions, and removing the template to produce a particle formed of the porous material, the particle having one or more holes extending between an interior region that is hollow and an external surface of the particle, the one or more holes having a size on the external surface substantially that of the surface area and distributed on the particle at the one or more regions.

Implementations can optionally include one or more of the following features. For example, the method further can include loading a substance into the interior region of the particle through the one or more holes, the substance incapable of passing through the porous material and forming an outer porous layer over the particle that permits selected particles to pass through, in which the outer porous layer seals the one or more holes of the particle, thereby enclosing the substance within the particle.

In another aspect, a nanoparticle device for carrying a load includes a shell structure including at least two layers including an internal layer and an external layer, the internal layer structured to enclose a hollow interior region and include one or more holes penetrating the internal layer, the external layer formed around the internal layer, in which the shell structure contains a substance within the hollow interior region, the substance having entered the shell structure through the one or more holes and is incapable of passing through the external layer.

In another aspect, a nanoparticle device includes a shell structure structured to include one or more holes extending between an interior region that is hollow and an external surface of the shell structure, and at least one central particle contained within the interior region and having a size larger than a size of each of the one or more holes, in which the one or more holes are structured to receive a substance that passes into the interior region and the substance binds to the at least one central particle.

In another aspect, a method of fabricating a particle includes combining a core particle with one or more masking particles to form a template, in which the one or more masking particles bind to the core particle and cover one or more regions of the surface of the core particle, each of the one or more regions corresponding to a surface area formed between each of the one or more masking particles and the core particle, forming a layer over the template, in which the layer forms over the surface of the core particle excluding the covered one or more regions, and removing the template to produce a shell structure having one or more holes extending between an interior region that is hollow and an external surface, the one or more holes having a size on the external surface substantially that of the surface area and distributed on the shell structure at the one or more regions.

Implementations can optionally include one or more of the following features. For example, the method can further include loading a substance into the interior region of the shell structure through the one or more holes and forming an outer layer over the shell structure, in which the outer layer seals the one or more holes of the shell structure and encloses the substance within the interior region.

In another aspect, a nanoparticle device includes a shell structure including at least two layers including an internal layer and an external layer, the internal layer structured to enclose a hollow interior region and include one or more holes penetrating the internal layer, the external layer is of a porous material and formed around the internal layer and sealing the one or more holes, and a substance contained within the hollow interior region, the substance incapable of passing through the external layer.

The subject matter described in this patent document can be implemented in specific ways that provide one or more of the following features. For example, the disclosed nano- and micro-structures can include nanoparticles having sealable holes to a hollowed interior that can encapsulate other substances contained inside the hollow region. For example, the exemplary hollow nanoparticles with sealable holes can further include pores that permit transport of selected particles or substances, while not permitting transport of the encapsulated substances. Exemplary methods to fabricate the disclosed nanoparticles (e.g., the exemplary hollow porous nanoparticles (HPNPs)) are described offering precise control and flexibility over the size and permeability of the nanoparticles, e.g., using a variety of materials. The described nano- and micro-structures include exemplary features including, for example, a high characteristic surface area and hollow interior capable for loading substances, which can enable implementations in a broad range of applications, e.g., including nanomedicine, catalysis, optics, waste removal, among many other applications. The disclosed nano- and micro-structures can be applied to medical diagnostics, monitoring and therapy, e.g., such as prodrug-enzyme therapy, enzyme or gene delivery and sensor applications. Exemplary nanomedicine applications can include controlled release of drugs, biological molecules and chemicals, immuno-isolation and protection of biomolecules and biologically active species, building blocks for photonic crystals, and removal of waste substances. For example, one or more macromolecules or macromolecular system(s) can be encapsulated in an exemplary HPNP and be sealed afterwards, e.g., forming a sealed hollow porous nanoparticle (SHPNP), after which the exemplary macromolecule(s) can still be in communication with the environment, e.g., via small molecules that can traffic in and out through the pores of the SHPNP.

In an example of an application using the disclosed technology, the exemplary macromolecule encapsulated in the exemplary SHPNP can be a molecule capable of signaling the occurrence of a particular event such as pH change. When pH changes in the environment, the pH change can be detected by the exemplary encapsulated macromolecule, e.g., because ions can move through the pores of the exemplary SHPNP. For example, in this configuration, the exemplary macromolecule used to detect the pH change is not introduced to the environment and therefore does not activate any immune response. Similarly, the exemplary SHPNPs can be used for different applications, e.g., in which the encapsulated structure is an enzyme. For example, an enzyme can be encapsulated in an SHPNP and be used to activate a drug molecule, e.g., which it binds to that would be otherwise deactivated. The exemplary enzyme is protected inside the exemplary SHPNP from the immune system, and the outside of the exemplary SHPNP can be conjugated to targeting agents to enable specific binding to a targeted site within the environment. Once the exemplary SHPNP having the encapsulated enzyme is delivered to the target site (e.g., tumor), a deactivated drug can be introduced into the blood flow of the organism (e.g., since the drug is deactivated, there is no limitation of drug dose). Also, for example, since the drug is a small particle, it can diffuse to many regions associated with the target site. However, the drug can be activated only at the region having the exemplary enzyme-encapsulated SHPNP, e.g., which can be targeted to that particular site or region. Therefore, in this example, the drug is only activated at the target site, e.g., by moving through the SHPNP pores and interacting with the encapsulated enzyme (e.g., activating the drug), and then moving out through the SHPNP pores to treat the tumor. For example, drug delivery via the disclosed nanoparticles can be used to provide stabilization, extended circulation, and targeting. In other examples, the encapsulated load can include proteins responsible for activating a certain mechanism, other nanoparticles, and/or toxic substances, e.g., protected from the biological environment that the exemplary SHPNPs are deployed.

BRIEF DESCRIPTION OF THE DRAWINGS

FIGS. 8A-8I show electron micrographs of exemplary hollow porous silica nanoparticles.

FIGS. 10C-10E show electron micrographs showing exemplary nanoparticles.

FIG. 11 shows an image demonstrating in vivo activity in the disclosed technology.

Like reference symbols and designations in the various drawings indicate like elements.

DETAILED DESCRIPTION

Nanostructures such as nanoparticles can be used to carry chemical or biological substances (e.g., drugs) as loads and be deployed for delivery of the loaded substances in a variety of environments, including biological environments such as within an organism. For example, nanostructure carriers deployed in an in vivo environment can themselves trigger an immune response and/or cause toxicity issues, e.g. which can be due to the nanoparticle carrier material and/or the loaded substance material. In some cases, drug delivery systems via nanoparticles can require modification of the loaded substance, which can reduce the desired function of the loaded substance.

Techniques, systems, and devices are described for fabricating and implementing nanoparticles that include a hollow core and sealable holes.

The disclosed nanoparticles and nanoparticle systems can include a hollow nanoparticle-based carrier platform that is capable of encapsulating and protecting substances within an interior region of the nanoparticle, e.g., through sealable holes. For example, the disclosed nanoparticle-based carrier platform can include hollow porous nanoparticles that can enclose a molecular load such that it is hidden from the immune system within its hollow core, while allowing controlled interaction of the enclosed load within the desired environment, e.g., via pores on the surface that lead to the interior region of the nanoparticle. For example, the exemplary hollow porous nanoparticles can themselves be biocompatible, but encase a non-biocompatible load. For example, implementation using the disclosed nanoparticles and nanoparticle systems in some applications can eliminate the need for modifying a payload substance, prevent triggering of an undesired immune response when deployed in an organism, allow flexible surface functionalization of the nanoparticle (e.g., for targeting), or extend circulation lifetime of the nanoparticles independent of the loaded substance(s). Also for example, the disclosed nanoparticles and nanoparticle systems can include a hollow non-porous nanoparticle-based carrier platform that is capable of encapsulating and protecting substances within the interior region of the nanoparticle through sealable holes and release the encapsulated substances into an environment that the nanoparticle is deployed, e.g., in which the sealable holes can dissolve and release the load in the deployed environment. In other examples, the disclosed nanoparticles and nanoparticle systems can include a hollow nanoparticle-based carrier platform that is capable of encapsulating and protecting substances within the interior region of the nanoparticle through sealable holes and release the encapsulated substances into an environment that the nanoparticle is deployed, e.g., in the nanoparticle can dissolve and release the load in the deployed environment.

In one aspect, the disclosed technology includes fabrication techniques that can be used to create nano-scale structures (e.g., such as nano-cage or nano-shell particles) having sealable holes and small pores, each of controllable sizes, e.g., in which the structure can encapsulate other substances contained within an interior region. Described are fabrication methods that can produce hollow porous nanoparticle (HPNPs) having holes configured to a controllable size, e.g., which can allow entry of other substances or particles (e.g., macromolecules) within its hollow interior. The described fabrication methods include techniques to seal the holes of the HPNPs, e.g., forming sealed hollow porous nanoparticles (SHPNPs), which can enclose the loaded substances or particles within the SHPNPs. For example, to fabricate HPNPs, a core particle is used as a starting template material, e.g., which can be in the form of any shape, including a sphere, cone, rod, rectangular solid, tube, among others. Masking particles can bind to the external surface of the template material, e.g., by intermolecular interactions. A porous shell can be formed by applying a coating material around the template material forming a core shell nanoparticle. Afterwards, the core and bound masking particles can be removed, e.g., by dissolution or calcination or other similar methods, in which the porous shell remains. Implementation of this process can form hollow porous nanoparticles, and other molecules can be encapsulated inside the interior of the produced nanoparticle. For example, the described fabrication methods can include techniques to load and seal the holes completely, e.g., once the exemplary macromolecules are encapsulated inside, enabling the porous shell particle as a loaded carrier. For example, the hole size can be adjusted independent of the size of the nanoparticle size. For example, the described fabrication methods can include techniques to independently adjust the pore size.

Exemplary template-based techniques are described that can use a variety of materials (e.g., including polymers, ceramics, and metals) to prepare HPNPs with monodisperse sizes, e.g., ranging from several tens of nanometers to micrometers in core particle diameter. The exemplary template-based techniques can be used to produce surface holes of controllable sizes along the hollow particle shell, e.g., ranging from a few nanometers to tens or hundreds of nanometers in hole diameter. The described fabrication techniques can provide independent control of the permeability of HPNPs. For example, permeability of the HPNPs can be configured by controlling the porosity of the shell material, e.g., producing pores of sizes that can range from a few to several nanometers. For example, nanometer pore sizes can result in relatively low permeability of large macromolecules diffusion into/out of the HPNPs, e.g., preventing enzymes, proteins or larger biologically active materials to diffuse through the HPNP while still permitting smaller substances to diffuse through the pores. For example, exemplary implementations using silica and gold HPNPs are described demonstrating precise control of particle size and surface porosity. The described fabrication techniques can be modified to produce HPNPs of different materials, e.g., including, but not limited to, calcium-based nanoparticles such as calcium phosphate or calcium coated particles, iron oxide nanoparticles, among other materials. For example, fabricating HPNPs of different materials can provide engineering of the properties of the HPNPs that can be suitable for particular desired applications.

The exemplary techniques can include colloidal templating reactions on surfaces with different chemical and physical properties. For example, a layer of shell material is grown over a colloidal particle template with parts of the surface blocked by smaller masking colloidal particles. Subsequently, the template and masking particles are removed by methods such as, for example, calcination and/or dissolution, to leave the hollow particle with open holes on the surface. For example, the overall size of the particle is determined by the template particle. For example, the diameter of the holes can be adjusted by varying the size of the masking particles, and the number of holes on the particle surface can be controlled by the relative molar concentration of template and masking particles.

The disclosed technology includes several protocols for fabricating the nanoparticles with hollow core, porous surface and sealable holes. FIGS. 1A-1C show schematic diagrams illustrating one exemplary nanoparticle synthesis protocol.

FIG. 1A shows an example of a process 110 in which masking particles 115 are mixed together with one or more core or template particles 111. For example, the masking particles 115 can be nanoparticles configured to have a surface charge, e.g., a negative surface charge. Also, for example, the masking particles 115 can include particles with a functionalized external surface 116, e.g., having a surface charge. For example, the exemplary masking particles 115 can be polystyrene nanoparticles, and the exemplary functionalized surface 116 can be a carboxylated-functional layer. For example, the template particle 111 can be a nanoparticle configured to have a surface charge, e.g., a positive surface charge, of opposite polarity to the surface charge of the masking particles 115. Also, for example, the template particle 111 can include a particle with a functionalized external surface 112. For example, the exemplary template particle 111 can be a polystyrene nanoparticle, and the exemplary functionalized surface 112 can be an amine-functional layer. For example, once the exemplary carboxylated masking particles 115 and aminated template particle 111 are mixed, the carboxylated particles 115 can bind to the aminated template particle 111.

Figure 1A:
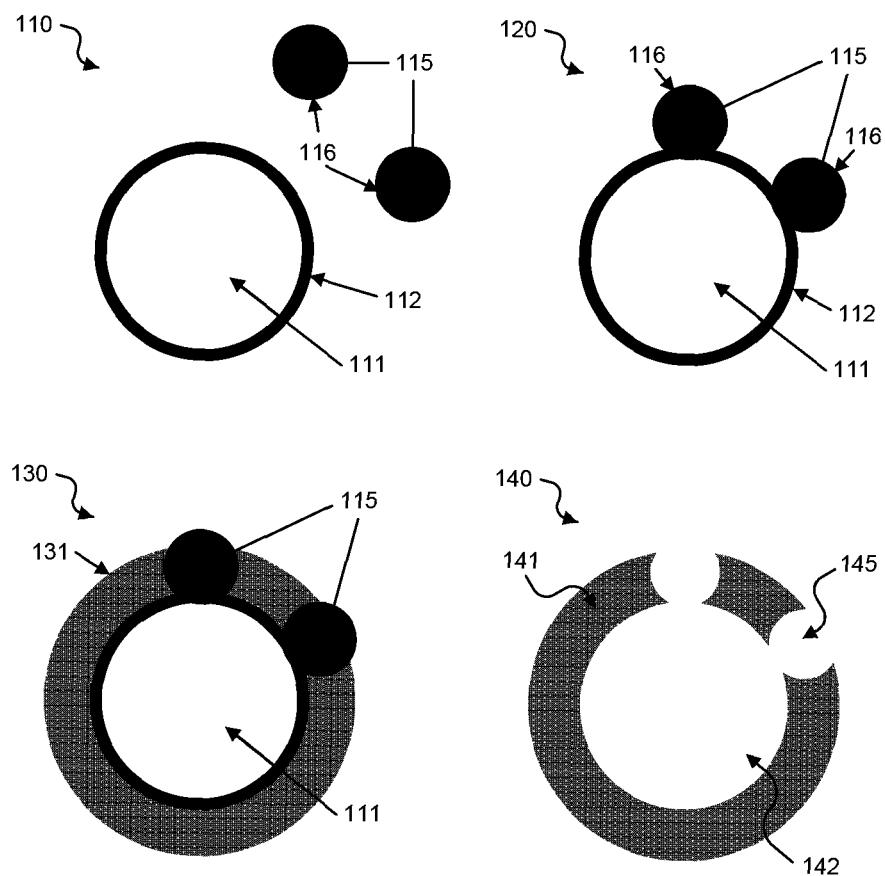
FIGS. 1A-1C show schematic diagrams illustrating an exemplary nanoparticle synthesis protocol.

FIG. 1A also shows an example of a process 120 of binding of the masking particles 115 with the carboxylated functionalized surface 116 to the aminated functionalized surface 112 of the template particle 111, e.g., by electrostatic interactions. For example, when the exemplary carboxylated particles 115 have a negatively charged surface, they repel negative ions and prevent sol-gel reaction on their surfaces, e.g., blocking some positively charged regions of the outer surface of the exemplary aminated template particle 111. In other examples, the process 120 can include binding the masking particles 115 to the surface 112 of the template particle 111 by other particle attraction means, e.g., including, but not limited to, hydrogen bonding, covalent bonding, magnetic attraction, hydrophobic interactions, etc.

FIG. 1A further shows an example of a process 130 of adding a layer 131 to the masking particles 115-template particle 111 complex. For example, sol-gel reagents can be added to the solutions containing the masking particles 115 bound to the template particles 111. Exemplary sol-gel reactions can occur only in the positively charged regions along the surface 112 of the template particle 111, e.g., the regions that are not covered or blocked by the masking particles 115. For example, the process 130 can cover the exposed surface of the template particle 111 with the coating 131 while not covering locations where the masking particles 115 are present. For example, the coating 131 can be a porous material. For example, the layer 131 can be of a material (e.g., silica) such that the process 130 can result in a porous layer forming on the surface of the template particle 111. For example, addition of sol-gel reactants in the process 130 can initiate silica growth, e.g., rooted from the amino groups of the exemplary aminated functionalized surface 112. Also for examples, the coating 131 can be a non-porous material. In some examples, the process 130 can include adding the layer 131 to the masking particles 115-template particle 111 complex by other means, e.g., including, but not limited to, material based exclusivity, or redox chemistry that forms the layer 131 only on the surface of one particle (e.g., the template particle 111) and not the surface of the other particle(s) (e.g., the masking particles 115), among other techniques. Exemplary materials used for the coating can include porous or non-porous materials, or degradable materials (e.g., that can dissolve or degrade in certain environments or under particular conditions or by an exemplary trigger, e.g., conditions and/or trigger including pH, temperature, pressure, molecular interaction, or other conditions and/or triggers).

In addition, FIG. 1A shows an example of a process 140 of forming a hollow nanoparticle, e.g., by removing the template particle 111 and the masking particles 115. For example, once the layer 131 is formed with the desired thickness, the template particle 111 and masking particles 115 are removed, e.g., by various methods including dissolving them by solvents, calcination, melting, or burning, or a combination of these or other similar methods. For example, the process 140 can include introducing dimethylformamide (DMF), acetone, or other solvent and/or heat to the layer-covered masking particles 115-template particle 111 complex. For example, implementation of the process 140 yields an HPNP that includes empty or hollowed porous shell 141 with holes 145 and an empty or hollowed interior 142, e.g., when the layer 131 is formed of a porous material. In some examples, the process 140 can be implemented to form a hollow non-porous nanoparticle, e.g., by removing the template particle 111 and the masking particles 115. For example, a hollow non-porous nanoparticle can be formed by implementing the process 130 using an exemplary non-porous material as the coating 131. In such examples, the exemplary shell 141 is a hollowed non-porous shell.

Once the exemplary HPNPs are created, they can be loaded with other substances and sealed to encapsulate the loaded substances.

Figure 1B:
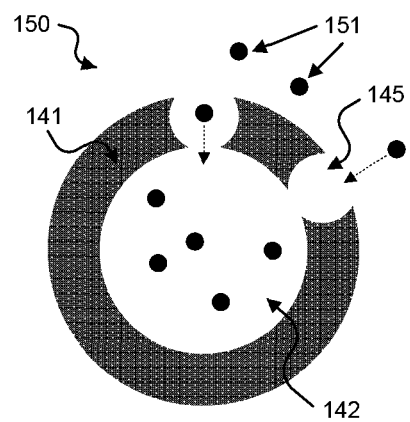

FIG. 1B shows an example of a process 150 for loading load particles 151 into the hollow interior region 142 of the shell structure 141. For example, a solution of shell structures (e.g., HPNPs) can be loaded with the load substances by adding a high concentration solution of the load substances to the solution of the shell structures. The process 150 can be implemented by one of several methods. For example, the load particles 151 can diffuse into the shell structures 141 through the holes 145. In other examples, the load particles 151 can enter the interior region 142 of the shell structures 141 through their holes 145 by non-diffusion means, e.g., including electrophoretic forces. The process 150 can be implemented using various types of materials as the load, e.g., including, but not limited to, drugs, biodegradable macromolecules, pH sensitive molecules, enzymes, hormones, and/or other proteins, glycoproteins, glycolipids, carbohydrates, lipids, nucleic acid, aptamer, metals, polymers, and ceramic particles, for various applications.

Figure 1C:
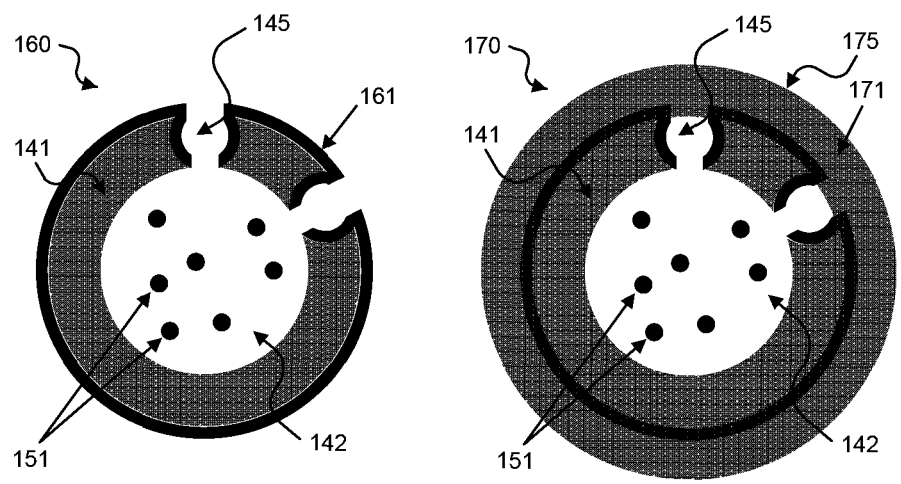

After loading the shell structures 141 with the load particles 151, the holes 145 can be sealed. FIG. 1C shows processes 160 and 170 showing forming a sealed hollow porous nanoparticle 175, e.g., by sealing the holes 145 of the exemplary HPNP 141 that encloses the load particles 151 within the hollow interior region 142. In this example, the holes 145 can be sealed with a further layer of a porous material (e.g., silica) shown as layer 171. In other examples, the holes 145 can be sealed with a further layer of a non-porous material (e.g., a metal layer or other non-porous material), which can also be represented by the layer 171.

The process 160 can include partially covering the holes 145 with a layer 161 (e.g., a large positively charged polymer such as poly-L-lysine (PLL)). For example, the PLL polymer can create a mesh like structure over the surface of the exemplary HPNP 141 and the holes 145. The process 170 can include sealing the load particles 151 within the exemplary HPNP 141 to form a sealed hollow porous nanoparticle 175. For example, the process 170 can include forming a layer 171 over the exemplary PLL-covered HPNP 141. For example, further addition of sol-gel reactants can create another layer (e.g., the layer 171) on top of the initial layer (e.g., the layer 161) covering the holes 145, e.g., by nucleation sites that are on the exemplary PLL polymer, thereby forming the exemplary SHPNP 175. For example, the exemplary load particles 151 can be permanently sealed and enclosed inside the exemplary SHPNP 175. In some examples, the process 170 can be implemented to form the exemplary sealed hollow porous nanoparticle 175 without implementing the process 160, e.g., by forming a layer 171 directly over the exemplary shell structure 141. In some example, a sealed hollow non-porous nanoparticle can be formed by implementing the processes 160 and 170 using an exemplary non-porous material as the coating 131. In such examples, the exemplary shell 141 is a hollowed non-porous shell (e.g., with the load particles 151 inside the hollow interior region 142) that can be covered with the layer 161 (e.g., a large positively charged material, forming a mesh-like structure over the surface of the exemplary shell structure 141 and the holes 145), and the holes 145 can be sealed (e.g., enclosing the load particles 151 within the exemplary shell structure 141) by forming the layer 171 over the exemplary layer 161-covered shell structure 141, thereby forming the exemplary sealed hollow nanoparticle 175. In this example, the exemplary sealed hollow nanoparticle 175 can include a non-porous layer 141 and a porous layer 171, e.g., in which small particles or substances can traffic in and out of the exemplary nanoparticle 175. Also in such examples, the process 170 can be implemented to form the exemplary sealed hollow nanoparticle 175 without implementing the process 160, e.g., by forming a layer 171 directly over the exemplary shell structure 141 (e.g., loaded with the load particles 151 inside the hollow interior region 142).

For example, the process 170 can include determining a material for the layer 171 can be based on a desired application. In some examples, the exemplary sealed hollow nanoparticle 175 can include a porous layer 141 and a porous layer 171. In other examples, the exemplary sealed hollow nanoparticle 175 can include a non-porous layer 141 and a porous layer 171. In other examples, the exemplary sealed hollow nanoparticle 175 can include a porous layer 141 and a non-porous layer 171. And in other examples, the exemplary sealed hollow nanoparticle 175 can include a non-porous layer 141 and a non-porous layer 171.

Exemplary load particles 151 can include degradable materials (e.g., that can dissolve or degrade in certain environments or under particular conditions or by an exemplary trigger, e.g., conditions and/or trigger including pH, temperature, pressure, molecular interaction, or other conditions and/or triggers). For example, the exemplary sealed hollow nanoparticle 175 load particles 151 can be deployed in a particular environment, in which the exemplary load particles 151 (e.g., of a degradable material) can undergo degradation (e.g., based on the conditions of the particular environment) and be released outside the particle through pores of the exemplary SHPNP 175, or in some examples, in combination with degradation of the exemplary sealed hollow nanoparticle 175.

The exemplary fabrication process depicted in FIG. 1A can be implemented using polystyrene nanoparticles with amino functional groups as the exemplary template particles and polystyrene nanoparticles with carboxyl functional groups as the exemplary masking particles. For example, amino functional groups are positively charged and can facilitate the chemistry used in the exemplary fabrication process. In some examples, exemplary sol-gel reagents require a positively charged nucleation site, which can be provided by the aminated functionalized surface. Fabrication of exemplary HPNPs can be implemented using materials such as vesicular solution, colloids, emulsion droplets and polymers as templates for forming a layer of target material or its precursor. For example, the exemplary fabrication process can be implemented using silicic acid is used as a precursor. For example, silicic acid gives negatively charged silicon-containing ions to the solution. These exemplary negatively charged ions are attracted by the positively charged template nanoparticle surface. For example, silica can be selected as a coating material over the masked template surface; e.g., properties of silica can include adjustable porosity, thermal and mechanical stability, low density, high specific surface area, and biocompatibility and biodegradability, which can be important properties in medical- and biological-based applications.

Exemplary silica HPNPs were fabricated for use in exemplary implementations of the disclosed technology. For example, amine-functionalized polystyrene nanoparticles (APNPs) can be used as the template for nucleating growth of the nanoporous silica sol-gel network. For example, tetramethoxysilane (TMOS) is hydrolyzed in aqueous solution to give silicic acid, which acts as a precursor for the polycondensation reaction on the particle surface. Exemplary chemical reactions below describe the initial stages of the polycondensation reaction of silicic acid resulting in the growth of silica layer.

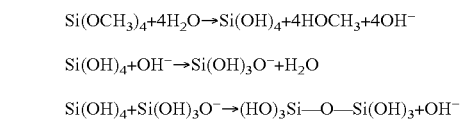

For example, the exemplary fabrication process can include mixing APNPs with carboxyl-functionalized polystyrene latex nanoparticles (CPNPs) in an aqueous solution (e.g., illustrated in the process 110 of FIG. 1A). The exemplary APNPs and CPNPs can aggregate together, e.g., due to electrostatic interaction of functional groups (e.g., illustrated in the process 120 of FIG. 1A). For example, the exemplary particles with oppositely charged surface functional groups attract each other in solution. For example, the amine functionalized surface creates a more efficient nucleation site for base-catalyzed silica gel growth compared to the acidic carboxyl-functionalized surface. At the point of contact, CPNPs serve as a negatively charged nanomask for the sol-gel reaction on the particle surface. The exemplary fabrication process can include adding silane to the solution to be hydrolyzed and give silicic acid, e.g., which acts as a precursor to the silica layer. For example, basic amine groups on the APNPs can template silica gel growth efficiently, whereas acidic carboxyl groups on the CPNPs can mask the reaction at point of contact with the APNPs (e.g., illustrated in the process 130 of FIG. 1A). The exemplary fabrication process can include removing the APNPs and CPNPs through, for example, calcination or dissolution. Once the silica layer is formed with the desired thickness, the polystyrene particles are removed by dissolution or calcination leaving the silica HPNP structure (e.g., illustrated in the process 140 of FIG. 1A). In some examples, the exemplary fabrication process can include resuspending and dispersing the HPNPs in water using vortex mixing and gentle sonication. For example, the final particle diameter after calcination can be approximately 85% of the diameter of the initial 500 nm template APNPs, which may be related to partial dehydration of the silica gel hydroxyl groups during heating or extraction with anhydrous solvents.

For example, the fabrication process can be implemented to produce silica shell particles (e.g., HPNP 141 in FIG. 1A, and SHPNP 175 in FIG. 1C) having pores that allow small molecules to get through. However, the large molecule load (e.g., load particles 151 shown in FIG. 1C) cannot get through the holes, and is therefore sealed within the particle. There can be other variations of this exemplary fabrication technique (described in FIGS. 1A-1C) that can be based on the desired application. For example, the HPNP can be formed of metal (e.g., such as gold), or there can be multiple or multiple varying layers of different materials that form the HPNP, e.g., such as a first internal layer of metal and a second external layer of polymer (e.g., silica). The size of the particle can be determined by the size of the template particle, and the sizes of the holes can be determined by the sizes of the blocking or masking particles. The size of the disclosed hollow porous nanoparticle and the size of its holes can be configured independent of each other. In addition, the porosity of the HPNP can be configured independent of the size of the HPNP and the size of its holes.

Figure 2A:
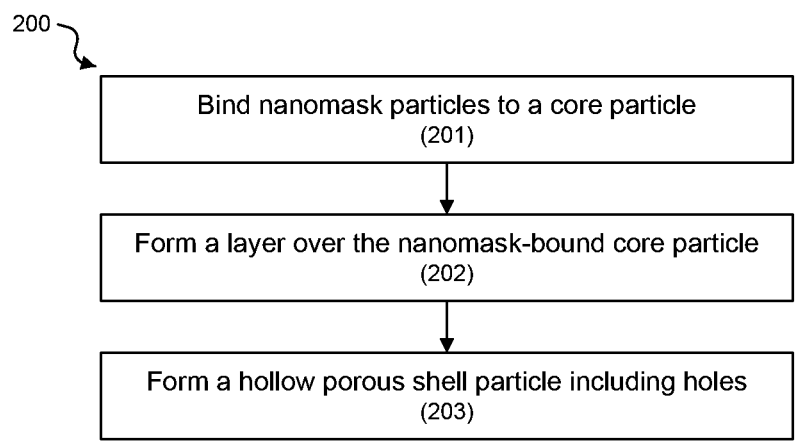
FIGS. 2A-2B show process diagrams of an exemplary nanoparticle synthesis protocol.
Figure 2B:
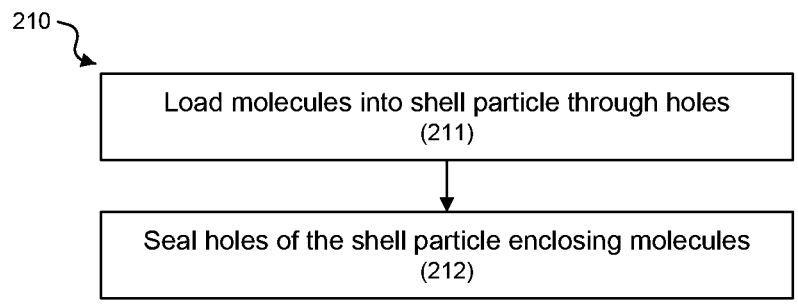

FIGS. 2A-2B show process diagrams of an exemplary synthesis protocol to produce hollow porous nanoparticles and sealed hollow porous nanoparticles. FIG. 2A shows a process diagram 200 that includes a process 201 to bind nanomask particles to a core particle, a process 202 to form a layer over the nanomask-bound core particle, and a process 203 to form a hollow porous shell particle including holes, e.g., by removing the nanomask particles and the core particle. FIG. 2B shows a process diagram 210 that includes a process 211 to load molecules or other substances into the hollow porous shell particle through the holes and a process 212 to seal the holes of the hollow porous shell particle to enclose the loaded molecules or other substances within.

The exemplary fabrication methods of the disclosed technology provide precise control of nanoporosity and particle diameter independently. For example, the exemplary fabrication methods can be applied to the broad range of materials accessible through sol-gel synthesis routes. In addition, the exemplary fabrication methods can be applied for different chemistries including gold and redox based chemistries, e.g., expanding the suitability of HPNPs to a broad range of applications.

Exemplary fabrication methods were employed using, e.g., tetramethoxysilane (TMOS) solution, which was obtained from Aldrich-Sigma Ltd. Exemplary chemicals were used as received. For example, amine functionalized polystyrene beads were obtained from Polysciences, Inc. and carboxyl-functionalized polystyrene latex particles were obtained from Life Technologies, Inc.

Exemplary implementations of the disclosed technology included the preparation of hollow porous silica nanospheres. For example, a 50 µL template particle solution was mixed with the corresponding amount of masking particle solution to prepare the desired ratio of particle concentrations. The resultant mixture was shaken overnight and 1000 µL of anhydrous ethanol was added to the solution. In order to generate the silica precursor and initiate the silica growth, 1 µL of tetramethoxysilane was added to the solution. The mixture was shaken overnight, and the suspended particles were collected by centrifugation (e.g., 5 min at 14000 rpm), washed with deionized water a few times and dried in vacuum overnight on a coverslide. To remove the organic compounds, a coverslide carrying the nanoparticle powder was placed over a hot plate and calcined overnight at 450° C. The calcined powder was transferred to a tube and suspended in water (e.g., 50 µL) and dispersed by gentle sonication.

Exemplary implementations of the disclosed technology included the preparation of sealed hollow porous silica nanospheres. For example, 4 µL of 10 mg/mL enzyme solution was added to 50 µL of the exemplary hollow porous silica nanospheres solution and incubated overnight. The exemplary solution was diluted with 1000 µL phosphate buffered saline and 50 µL 0.1% poly-L-lysine with a molecular weight of 150-300 kDa. For example, the exemplary solution can be diluted to prevent aggregation. TMOS was added to 1 mM HCl in 74:500 volume ratio and mixed for a few minutes to make silicic acid solution. 25 µL of the exemplary silicic acid solution was added to the above porous silica nanospheres solution immediately after the dilution and shaken for 1 hr, e.g., in order to generate sealed hollow porous silica nanospheres. Later, suspended sealed hollow porous silica nanospheres were collected with centrifugation (e.g., 5 min at 14000 rpm) and washed several times with water. Samples were exposed to proteinase-K enzyme overnight at a concentration of 0.1 mg/mL in 1× phosphate buffered saline (PBS) solution at 37° C., followed by removal of proteinase-K by successive washing again by 1× PBS by centrifugation (e.g., 5 min at 14000 rpm). The described protocol can be used for encapsulation of payload substances. For example, the payload substances utilized in the exemplary implementations included penicillinase and *Renilla reniformis* luciferase, e.g., encapsulated within exemplary hollow porous silica nanospheres.

For example, penicillinase from *Bacillus cereus* was obtained from Sigma-Aldrich Co., LLC. CCF2-AM was obtained from Life Technologies, Inc., San Diego, Calif., USA. Rabbit polyclonal biotinylated antibody was obtained from GeneTex, Inc., San Antonio, Tex., USA. All fluorescence intensities were measured on an Infinite 200 Pro, TECAN, Switzerland.

Exemplary implementations of the disclosed technology included the preparation of hollow silica nanospheres, in which a similar fabrication protocol to that of the described hollow porous silica nanospheres was implemented, except omitting nanomasks.

Exemplary implementations of the disclosed technology included the labeling of penicillinase with Cy5. For example, Cy5 maleimide was used as labeling agent for exemplary implementations demonstrating the described protocol. For example, 1 mg penicillinase was dissolved in 100 µL degassed PBS buffer at 10 mg/mL concentration. For example, thiol modifications were carried out under nitrogen in degassed solvents/buffers. The exemplary solution was left at room temperature for around 30 min. About 100 molar excess of TCEP was added to the exemplary solution. The vial was flushed with nitrogen gas, capped and mixed thoroughly. This reaction was incubated at room temperature for 10 min. 100 µg Cy5 maleimide was dissolved in 2 µL dimethylformamide (DMF) and added to the enzyme solution. The vial was again flushed with nitrogen, capped and mixed thoroughly. This solution was incubated at room temperature for 2 hr while being mixed every 30 min. Finally, the reaction was left overnight at 2-8° C. Later, unbound dye was removed by a desalting column with a molecular weight cut-off at 7 kDa.

The activity is measured in 100% normal mouse serum as the initial rate of increase of the ratio of blue fluorescence (447 nm) to green fluorescence (520 nm) with excitation at 409 nm.

The amount of enzyme loading (e.g., the exemplary Cy5 labeled penicillinase) was detected by measuring fluorescence intensity at 620 nm excitation and 665 nm emission.

Antibody binding was measured in the following exemplary manner. For example, anti-penicillinase was functionalized with biotin groups. Alexa 488 dye with streptavidin was added to all samples followed by successive washing. Fluorescence intensity measurements were performed at 480 nm excitation and 530 nm emission.

Exemplary implementations of the disclosed technology included in vivo activity measurements, which were prepared and performed in the following exemplary manner. For example, BALB/c mice were used in the exemplary implementations. For example, one mouse was injected with 100 µL of *Renilla reniformis* luciferase (RenLuc) enzyme encapsulated sealed hollow porous silica nanospheres solution intramuscularly. The exemplary sealed hollow porous silica nanospheres were suspended in 1× phosphate buffered saline (PBS) with a concentration of $5.68 \times 10^{12}$ particles/mL. For example, the other mouse was injected with 100 µL 8 µg/mL concentration of free RenLuc intramuscularly. Free RenLuc was suspended in 1× PBS. 5 minutes later, 10 µg benzyl-coelenterazine was administered intravenously in the lateral tail vein of each mouse. 10 µg benzyl-coelenterazine was dissolved in 95% ethanol and diluted with 1× PBS to 10% final concentration of alcohol. Mice were by isoflurane and luminescence intensities were measured from each mouse following intravenous injections with an exposure of 2 sec.

Exemplary implementations of the disclosed technology included the characterization of nanostructures. For example, SEM measurements were conducted on a FEI/Philips XL30 FEG ESEM, and ultra high resolution (UHR) SEM measurements were performed on FEI SFEG UHR SEM with acceleration voltages of 10 kV (e.g., at the UC San Diego, Calit2 Nano3 Facility). TEM images were obtained with the use of a FEI Technai Sphera 200 kV (e.g., UC San Diego, Cryo-Electron Microscopy). A Hitachi HD-2000 instrument was used for scanning transmission electron microscope (STEM) images operating at 200 kV. IVIS Imaging System 200 Series from Xenogen Corporation, Alameda, Calif. (e.g., at UC San Diego, Moores Cancer Center) was used for in vivo luminescence measurements.

Exemplary implementations performed are described that demonstrate precise control of the particle diameter, hole diameter, and hole concentration of exemplary silica hollow porous nanoparticles using the fabrication techniques of the disclosed technology. For example, the robustness and flexibility of the disclosed fabrication techniques offer the ability to implement the fabricated nanoparticles in a variety of common and unique applications in many fields.

Figure 3:
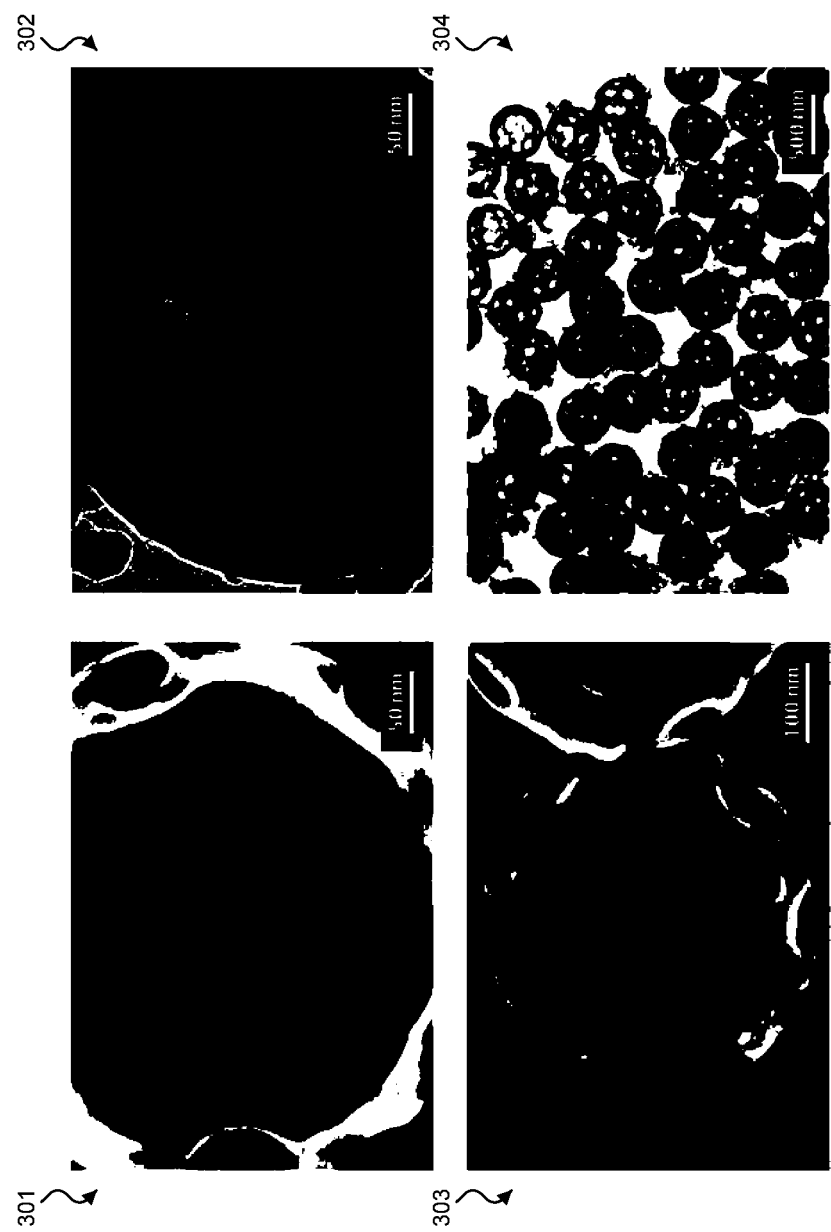
FIG. 3 shows exemplary transmission electron microscopy (TEM) images showing the structural properties of exemplary hollow porous nanoparticles.

High resolution electron micrographs are presented in FIG. 3 that reveal the structure of the generated holes. FIG. 3 shows exemplary transmission electron microscopy (TEM) images 301, 302, 303, and 304 exhibiting the structural properties of exemplary HPNPs. For example, the exemplary HPNPs can be generated by using 500 nm APNPs as template particles and 100 nm CPNPs as the masking or blocking particles. The image 301 shows a close-up view of the surface features of an exemplary HPNP, e.g., taken by secondary electron mode of scanning transmission electron microscope (STEM), which revealed the formation of 30±10 nm holes formed at the point of contact of the template and masking nanoparticles. The image 302 shows a TEM image of exemplary HPNPs displaying the hole structure and the thickness of the silica shell. The image 303 shows an SEM micrograph, e.g., taken with ultra high resolution mode, which shows the open-hole structure throughout the shell and the thickness of the shell from an interior perspective. The image 304 shows a wide field electron micrograph, e.g., taken by the transmission mode of STEM, which shows the monodispersity and evenness of exemplary uniform HPNPs. For example, the images of FIG. 3 show that silica formation is completely prevented around the point of contact between two particles and that the curvature of the masking CPNP surface is reflected by the surface topography of the resultant particle. For example, the exemplary synthesis using 500 nm APNP templates and TMOS to APNP weight ratio of 3:1 can result in silica shells with a thickness of 25 nm. This thickness can be related to yielding stable particles.

Figure 4:
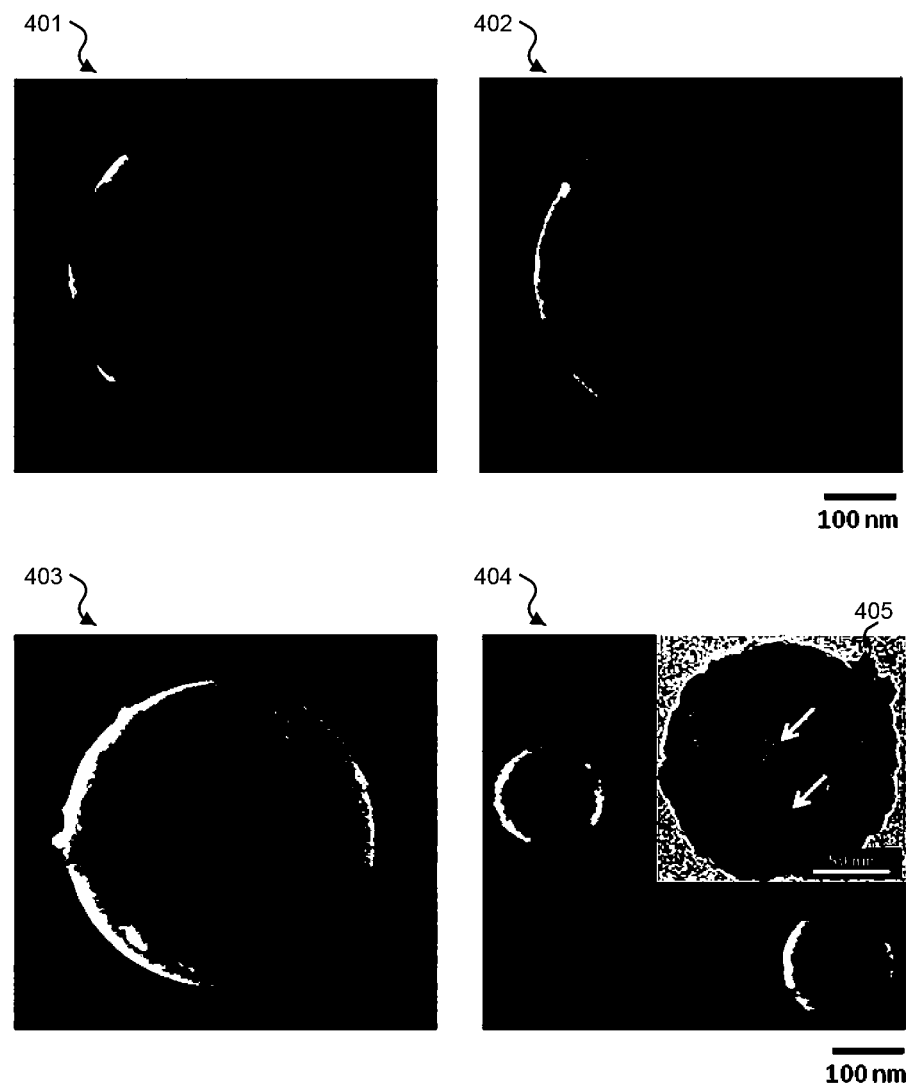
FIG. 4 shows scanning electron micrograph (SEM) images exhibiting degrees of freedom of the synthesis on exemplary hollow nanoparticle features.

FIG. 4 shows scanning electron micrograph (SEM) images 401, 402, 403, and 404 exhibiting degrees of freedom of the synthesis on exemplary HPNP features. The image 401 shows an exemplary HPNP surface exhibiting ~25-30 number of holes, e.g., by preparation using 500 nm APNP templating particles and 100 nm CPNP masking particles with a APNP-to-CPNP number ratio of 1:30. The image 402 shows an exemplary HPNP surface exhibiting ~10-15 number of holes, e.g., by preparation using the same templating and masking particles with a APNP-to-CPNP number ratio of 1:15 The image 403 shows a micrograph of HPNPs obtained using 500 nm APNPs and 40 nm CPNP taken by SEM. The image 404 shows an SEM image of HPNPs generated using 200 nm APNPs and 40 nm CPNP. The inset image 405 shows a higher resolution close-up TEM micrograph of these exemplary particles, e.g., where the exemplary arrows indicate the holes on the particle surface. The exemplary scale bar shown in the images 401, 402, 403, and 404 represents 100 nm, and the exemplary scale bar shown in the inset image 405 represents 50 nm.

The disclosed fabrication procedures can include multiple degrees of freedom in producing the HPNPs. For example, the exemplary fabrication process can include control of the number of holes on the surface (e.g., exemplified in the image 402), diameter of the holes (e.g., exemplified in the image 403) and overall particle size (e.g., exemplified in the image 404). For example, the average number of holes on the surface can be controlled by the relative molar concentration of the APNPs and CPNPs. SEM micrographs in the images 401 and 402 show the hole distribution on the surface when the APNP to CPNP molar ratios in solution are 1:30 and 1:15, respectively. The exemplary molar ratios of APNPs to CPNPs can result in ~25-30 holes per particle for the 1:30 ratio and ~10-15 holes per particle for the 1:15 ratio.

For example, the size of the holes created on the surface (e.g., hole diameter) can be adjusted by selecting masking CPNPs with different diameters independently of the overall diameter of the HPNPs. The exemplary hole size of the HPNPs shown in the image 401 include 30±6 nm diameter holes, e.g., created using CPNPs with a 100 nm diameter on 500 nm APNP. The exemplary hole size of the HPNPs shown in the image 402 include 20±3 nm diameter holes, e.g., created using CPNPs with a 60 nm diameter on 500 nm APNP. Exemplary CPNPs can be configured with diameters of ~20 nm to produce HPNPs with holes having a diameter of a few nanometers.

For example, the overall size of the HPNP depends on the template particle size. Exemplary APNPs can be configured in a wide range of sizes to prepare HPNPs, e.g., in ranges of ~30 nm to several micrometers. For example, HPNPs created by 500 nm APNP templates can shrink by about 15% upon template removal, e.g., resulting in HPNPs with diameters of 430 nm (as shown in the exemplary HPNP in the image 401). However, for example, the percent of shrinkage is not constant with changing APNP template size; in exemplary implementations, HPNPs fabricated by using 200 nm APNPs and 40 nm CPNPs resulted in an overall particle size of 150 nm corresponding to a shrinking by about 25% after calcination (as shown in the exemplary HPNP in the image 404). For example, increased shrinking may be explained by the higher relative volume ratio of the dehydrated hydroxyl groups to the total silica volume when using a smaller particle. Exemplary template and masking particle combinations resulted in holes about 25-35% of the diameter of the initial masking particles, e.g., decreasing slightly with smaller dimensions. For example, the slight decrease for smaller nanomasks may be related to increasing surface curvature resulting in a smaller point of contact. For example, a closer and higher resolution TEM micrograph shown in the inset image 405 of the 150 nm HPNPs includes arrows indicating the holes on the particle surface. For example, the diameter of the holes formed on the HPNPs fabricated using the 200 nm APNP/40 nm CPNP pair resulted in 12±2 nm.

Figure 5A:
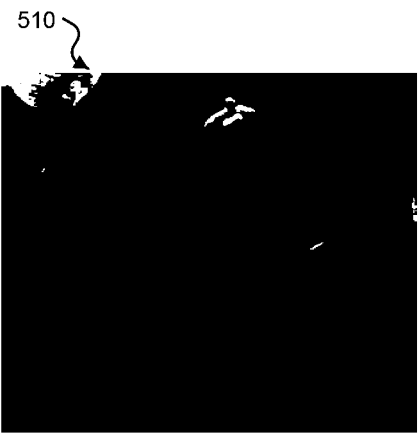
FIGS. 5A and 5B show an SEM image of exemplary aggregates and resultant hollow porous nanoparticles.
Figure 5B:
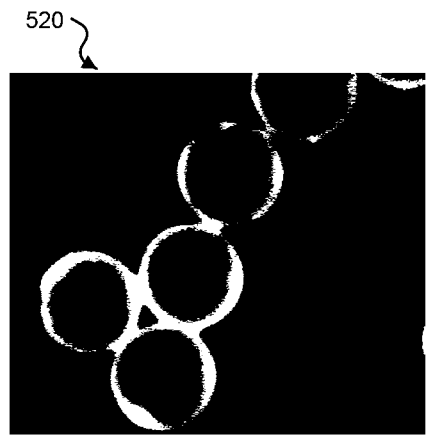

FIG. 5A shows an SEM image 510 of exemplary aggregates formed by 500 nm APNPs as template particles and 100 nm CPNPs as the masking or blocking particles. FIG. 5B shows an SEM image 520 of exemplary resultant HPNPs using the particle framework in the image 510. The exemplary scale bar shown in images 510 and 520 represents 200 nm.

Figure 5C:
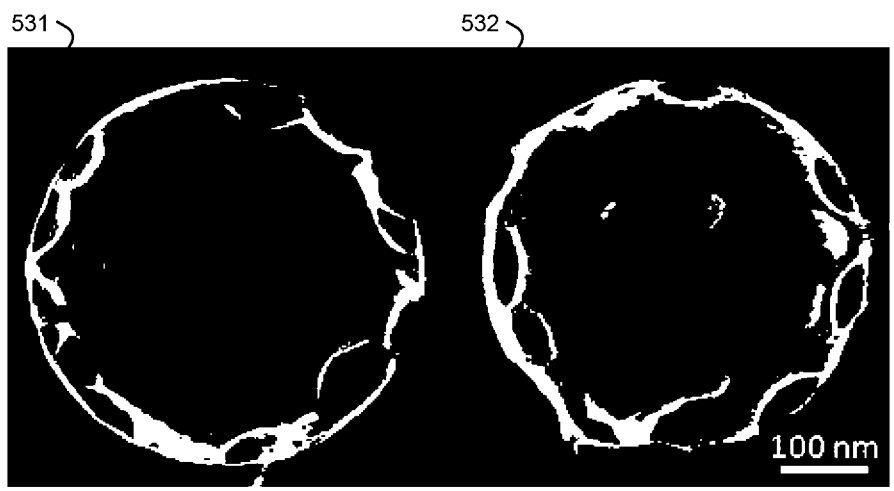
FIG. 5C shows SEM images of exemplary unsealed and sealed hollow porous nanoparticles.

FIG. 5C shows SEM images of exemplary unsealed HPNPs (shown in image 531) and sealed hollow porous nanoparticles (SHPNPs) (shown in image 532). The exemplary scale bar shown in FIG. 5C represents 100 nm.

The disclosed porous nanoparticles can be implemented in variety of applications, including very unique applications that may not be possible with any other method. For example, enzymes with non-human origin can be useful in a variety of therapeutic applications. However, immune responses, as well as proteolysis within endocytic organelles and organs of metabolic clearance, are generated against these foreign proteins and can hinder their therapeutic functionality.

In another aspect, the disclosed technology can include a porous shell based nano carrier platform that can encapsulate and protect a foreign macromolecular cargo from antibodies, proteases, and other biomolecules that may compromise the cargo's desired functionality. The described porous shell based nano carrier platform can also be referred to as HPNPs. For example, the porous shell based nano carrier platform can include hollow spherical nanoshells including holes (e.g., mesopores) that enable high-capacity loading of unmodified macromolecules, in which the loaded particles can be subsequently sealed with nanoporous material that still allows small molecules to easily diffuse in and out but prevents macromolecules from entering or leaving. The described sealed porous shell based nano carrier platform can also be referred to as SHPNPs.

The exemplary SHPNPs can be applied to in vivo medical diagnostics, monitoring and therapy, e.g., such as enzyme-prodrug therapy, enzyme replacement therapy, therapies based on enzymatic depletion of tumor nutrients, and in vivo biosensing. For example, since SHPNPs can be configured as thin hollow nanoshells, minimal inorganic mass is introduced while maximizing in vivo loading capacity. For example, the disclosed SHPNPs can be implemented to prevent immune response against their foreign enzymatic cargos and protect them from proteolysis. In this exemplary implementations, the SHPNPs can include nanopores (e.g., <2 nm diameter) on their surfaces for substrates to reach encapsulated enzymes within the hollow core interior, interact with and be modified by the enzymes, and diffuse out (as exemplified in FIG. 6).

Figure 6:
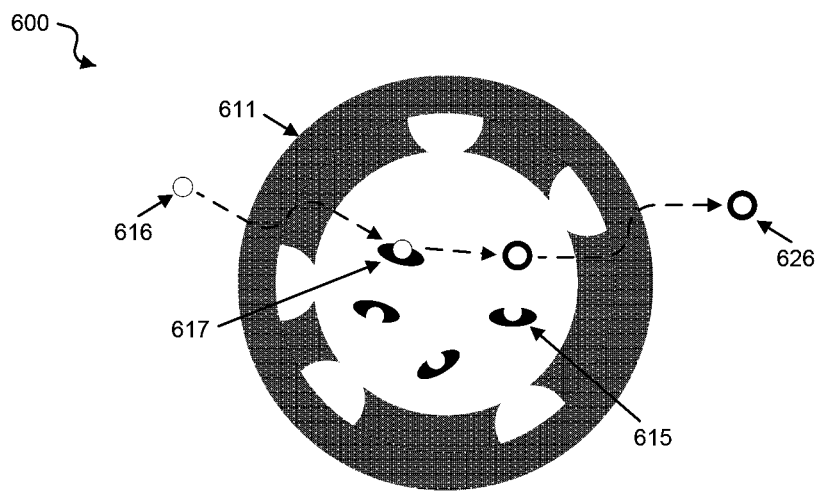
FIG. 6 shows an illustration of an exemplary implementation using the disclosed sealed hollow porous nanoparticles.

FIG. 6 shows a schematic diagram 600 illustrating the exemplary implementation of the disclosed sealed hollow porous nanoparticles having loaded enzymatic cargo for use in an enzyme-prodrug therapeutic application. The diagram 600 shows a sealed hollow porous nanoparticle 611 that encloses enzymes 615 within its hollow interior for interaction with prodrug molecules 616, the interaction occurring inside the SHPNP 611. For example, the enclosed enzymes 615 are protected inside the SHPNP 611, e.g., from the immune system or other substances in the environment in which the SHPNP 611 is deployed. For example, since the particle surface is porous, prodrug molecules 616 can diffuse into the SHPNP 611 and subsequently interact with the enzymes 615, e.g., depicted as prodrug-enzyme complex 617. For example, the enzyme 615 can be used to activate the prodrug molecule 616, e.g., which is otherwise deactivated. The interaction between the enzyme 615 and the prodrug 616 at the prodrug-enzyme complex 617 can result in the formation of an activated drug 626. The activated drug 626 can diffuse out of the SHPNP 611 and subsequently interact with a target that the drug is designed to treat.

Exemplary implementations of the SHPNP 611 can include deployment into a living organism for therapeutic drug delivery. For example, the external surface of the SHPNP 611 can be conjugated to targeting agents, e.g., to enable specific binding to a targeted site within the environment. For example, once the SHPNP 611 having the encapsulated enzyme 615 is delivered to a target site (e.g., tumor), a deactivated drug (e.g., the prodrug 616) can be introduced into the blood flow of the organism. Although the prodrug 616 can be exposed to a multitude of regions within the organism, the prodrug 616 can be activated only at the region having the exemplary enzyme-encapsulated SHPNP 611, e.g., which can be targeted to that particular site or region. Therefore, in this example, the prodrug 616 is only activated at the target site, e.g., by moving through the pores into the SHPNP 611 and interacting with the encapsulated enzyme 615 (e.g., activating the prodrug 616), and after which the activated drug 626 moving out through the pores into the SHPNP 611 to treat the exemplary tumor.

The fabrication of the exemplary SHPNPs (e.g., illustrated in the diagram 600) can be fabricated using the techniques previously described and shown in FIGS. 1A-1C, e.g., which include a high yield and scalable synthesis method that utilizes nanomasks preventing templating reaction on parts of the shell surface. For example, the described fabrication techniques lead to the formation of mesopores (e.g., which can range 2-50 nm) in HPNPs and SHPNPs for efficient loading of larger molecules, e.g., such as enzymes. For example, the exemplary HPNPs can be made from a shell of nanoporous material with mesopores on the surface allowing large biomolecules to diffuse into the hollow interior volume of the particles. For example, once large molecules of interest are loaded, the mesopores can be sealed with a nanoporous shell material (e.g., the same material used to form the HPNPs), thereby forming loaded SHPNPs.

For example, the surface of exemplary SHPNPs can be further functionalized for targeting and improved circulation half-life. The exemplary further functionalization of the SHPNPs can eliminate the need for any modification of the loaded substances. For example, under these conditions, stealth SHPNPs can be delivered to a targeted region and allow continuous and controlled access of a substrate to interact with the enzyme cargo within the protected environment of the SHPNPs, e.g., making them an ideal therapeutic platform for in vivo enzyme delivery for pro-drug therapies for diseases including cancer.

Figure 7A:
FIGS. 7A and 7B show SEM images of exemplary hollow porous nanoparticles.
Figure 7B:
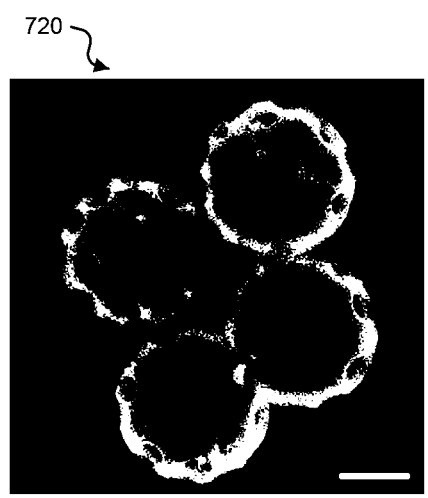

Exemplary SEM images of hollow porous nanoparticles are presented in FIGS. 7A and 7B, e.g., which demonstrate the implementation of the described HPNP synthesis techniques, e.g., previously described in FIG. 1A-1C. FIG. 7A shows an SEM image 710 of aggregated APNPs and CPNPs. For example, CPNPs are mixed with larger APNPs, and the CPNPs and APNPs having oppositely charged surface functional groups attract each other in solution causing aggregation. The image 710 demonstrates the framework for exemplary HPNP synthesis techniques showing 500 nm APNPs and 100 nm CPNPs. For example, the basic nature of the amine-functionalized surface can create a more efficient nucleation site for base-catalyzed silica gel growth compared to the acidic carboxyl-functionalized surface. For example, at the point of contact, CPNPs serve as negatively charged nanomasks for the sol-gel reaction on the particle surface. For example, once the silica layer is formed with the desired thickness, the polystyrene particles are removed leaving the silica hollow porous nanoparticle structure. FIG. 7B shows an SEM image 720 of silica hollow porous nanoparticles. For example, the final HPNP diameter after calcination is shown in the image 720 at about 85% of the diameter of the initial 500 nm template APNPs (as shown in the image 710), e.g., which may be related to partial dehydration of the silica gel hydroxyl groups during heating or extraction with anhydrous solvents. The exemplary scale bar represents 200 nm in the images 710 and 720.

Structural properties of the described hollow porous nanoparticles are shown in FIGS. 8A-8I. FIGS. 8A-8I include electron micrographs of silica HPNPs made from 500 nm templates and 100 nm nanomasks. FIG. 8A shows an electron micrograph 801 revealing the surface topography of an exemplary hollow porous nanoparticles taken with secondary electron mode of STEM. For example, the image 801 shows that silica formation is completely prevented around the point of contact between two particles and the curvature of the masking CPNP surface, which is reflected by the surface topography of the resultant particle. FIG. 8B shows a transmission electron micrograph 802 of an exemplary HPNP. For example, the exemplary synthesis technique using 500 nm APNP templates and TMOS to APNP weight ratio of 3:1 produced silica shells with a thickness of 25 nm. This exemplary thickness can yield stable particles in this size range. FIG. 8C shows a scanning electron microscope image 803 of an exemplary cracked HPNP showing the open-hole structure from an interior perspective. FIG. 8D shows an electron micrograph 804 taken with transmission mode of STEM showing the monodispersity of exemplary HPNPs.

The disclosed fabrication procedures can be applied to particles with different features in a wide range of sizes. For example, three degrees of freedom in the fabrication of HPNPs can include the number of holes on the surface, the diameter of the holes, and the overall particle size. FIG. 8E shows an SEM image 805 showing an exemplary HPNP formed by 500 nm templates and 100 nm nanomasks, e.g., with the particle number ratio of 1:30. FIG. 8F shows an SEM image 806 showing an exemplary HPNP formed by 500 nm templates and 100 nm nanomasks with the particle number ratio of 1:15. For example, the average number of holes on the surface is controlled by the relative molar concentration of the APNPs and CPNPs. SEM micrographs in FIGS. 8E and 8F show the hole distribution on the surface when the APNP to CPNP molar ratios in solution are 1:30 and 1:15, respectively. These ratios result in 25-30 holes per particle for the 1:30 ratio (e.g., shown in FIG. 8E) and 10-15 holes per particle for the 1:15 ratio (e.g., shown in FIG. 8F). FIG. 8G shows an SEM image 807 showing an exemplary HPNP formed by 500 nm templates and 60 nm nanomasks. For example, the size of the holes created on the surface can be adjusted by selecting masking CPNPs with different diameters independently of the overall diameter of the HPNP. The use of 100 nm masking CPNPs can produce holes of 30±4 nm in diameter (e.g., shown in FIGS. 8E and 8F), and the use of 60 nm masking CPNPs can produce holes of 20±3 nm in diameter at the point of contact (e.g., shown in FIG. 8G). Exemplary CPNPs can be used having a 20 nm in diameter, e.g., yielding holes down to several nanometers with high accuracy.

FIG. 8H shows an SEM image 808 showing an exemplary HPNP formed by 200 nm templates and 40 nm nanomasks. For example, the overall size of the HPNP can be configured based on the template particle size. The exemplary HPNPs created by 500 nm APNP templates were shown to reduce in diameter by about 15% upon template removal resulting in HPNPs with diameters of 430 nm (e.g., shown in FIGS. 8E-8G). However, the percent of shrinkage is not constant with changing APNP template size; e.g., exemplary HPNPs generated by using 200 nm APNPs and 40 nm CPNPs resulted in an overall particle size of 150 nm corresponding to a shrinking about 25% after calcination (e.g., shown in FIG. 8H). For example, increased shrinking may be due to the higher relative volume ratio of the surface hydroxyl groups to the total silica volume when using a smaller particle. The exemplary scale bar represents 50 nm in the image 808.

Exemplary implementations performed showed that template and nanomask particle combinations resulted in holes (e.g., mesopores) about 25-35% of the diameter of the initial nanomasks, e.g., decreasing slightly with smaller dimensions. For example, the slight decrease for smaller nanomasks may be related to increasing surface curvature resulting in a smaller point of contact. FIG. 8I shows a TEM image 809 showing an exemplary HPNP of a 150 nm diameter. The exemplary arrows shown in the image 809 indicate holes on the surface. For example, the diameter of the holes was shown to be 12±2 nm, and the exemplary HPNP was formed by 200 nm APNPs and 40 nm CPNPs. The exemplary scale bar represents 50 nm in the image 809.

Figure 9A:
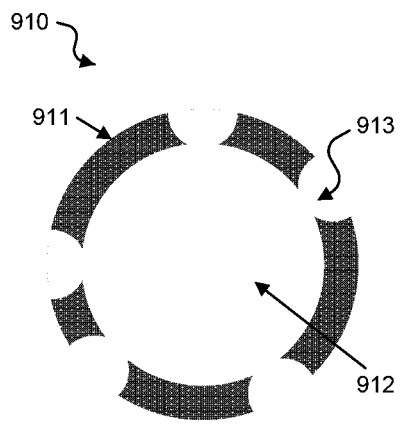
FIGS. 9A-9D show schematic illustrations of an exemplary fabrication process to create sealed hollow porous nanoparticles.
Figure 9B:
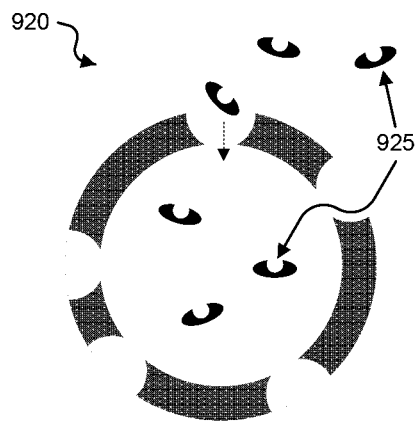
Figure 9C:
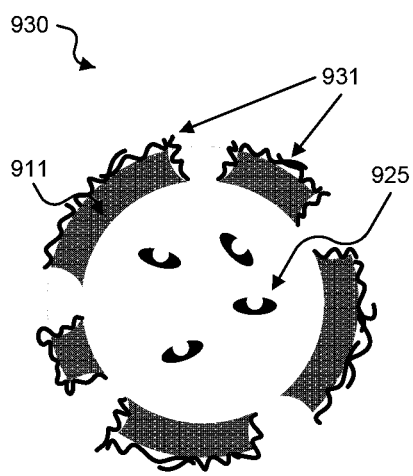
Figure 9D:
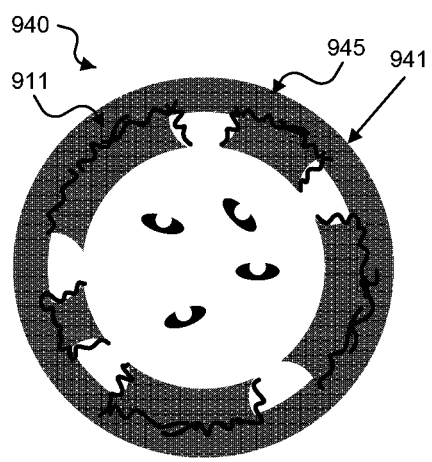
Figure 10A:
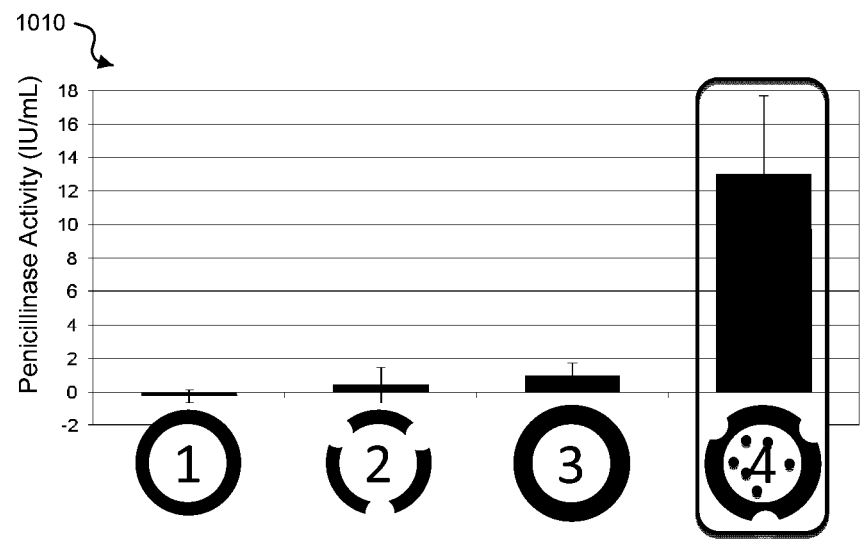
FIGS. 10A and 10B show data plots showing activity of sealed hollow porous nanoparticles of the disclosed technology.
Figure 10B:
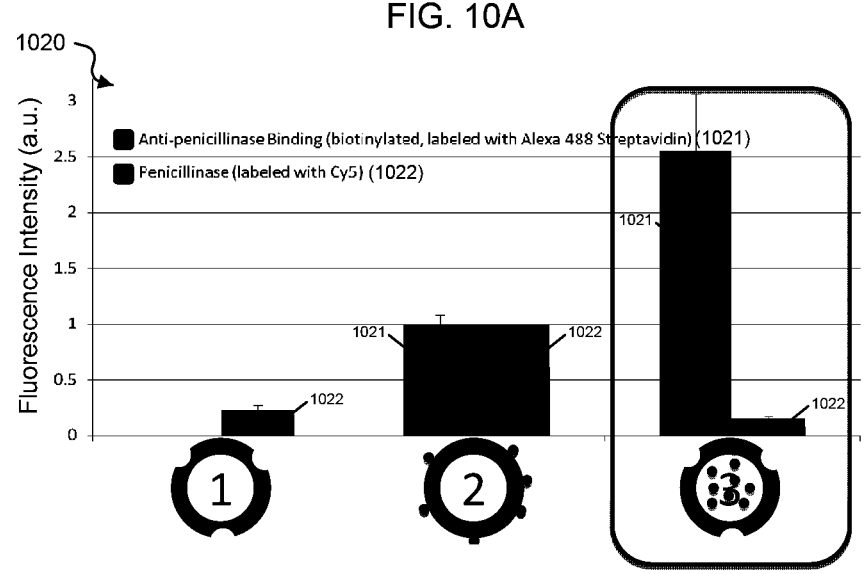

FIGS. 9A-9D show schematic illustrations of an exemplary fabrication technique of SHPNPs. FIG. 9A shows a process 910 of producing an HPNP 911 including a hollow interior core 912 and holes 913 (e.g., mesopores) extending through the exterior shell of the HPNP 911 to the hollow interior core 912. For example, the HPNP 911 can include small pores that permit traffic of small molecules in and out of the HPNP 911. For example, the process 910 can include the implementation of the processes 110, 120, 130, and 140 to produce the HPNP 911. FIG. 9B shows a process 920 of loading enzymes 925 into the HPNP 911. For example, the process 920 can include adding a high concentration of a solution containing the enzymes 925 to a solution containing the HPNPs 911 (e.g., which can be in an HPNP suspension). For example, the process 920 can include the enzymes 925 diffusing into the hollow interior 912 of the HPNP 911 through the holes 913 by diffusion. For example, since the holes are relatively large compared to the enzymes, the enzymes 925 can freely diffuse into the structure quickly, equilibrating the concentration inside and outside of the HPNPs 911. In other examples, the process 920 can load the enzymes 925 into the hollow interior 912 of the HPNP 911 through the holes 913 by electrophoretic forces. FIG. 9C shows a process 930 of partially covering the holes 913 and the surface of the HPNP 911 with a layer 931. For example, the process 930 can include a depositing a large positively charged polymer such as PLL. For example, the layer 931 can be configured as a PLL polymer layer that can create a mesh like structure over the surface of the HPNP 911 and the holes 913. FIG. 9D shows a process 940 of sealing the enzymes 925 within the HPNP 911 to form a sealed hollow porous nanoparticle 945. For example, the process 940 can include forming a layer 941 over the layer-covered HPNP 911. For example, further addition of sol-gel reactants can create another layer (e.g., the layer 941) on top of the initial layer (e.g., the layer 931) covering the holes 913, e.g., by nucleation sites that are on the exemplary PLL polymer, thereby enclosing the enzymes 925 within the SHPNP 945.

For example, in the case of a silica HPNP, the surface of the HPNP 911 is negatively charged due to $SiO^-$ groups. A positively charged polymer such as PLL can be added to adsorb to the particles' surface and change the surface charge to positive. Subsequently, TMOS can be added to grow a new layer of silica on the surface, e.g., closing the holes (e.g., mesopores) of the HPNP 911. This exemplary reaction can occur in near neutral buffer condition and does not damage the enzyme load. For example, once the mesopores are closed, the load is encapsulated within the SHPNP 945 and cannot escape. However, the load can still interact with small molecules in the surrounding environment via diffusion through nanopores.

This exemplary capability can be used to provide several benefits. For example, the exemplary enzyme load is hidden from the immune system, e.g., because antibodies are too large to pass through the nanopores to reach the enzyme. For example, the exemplary enzyme load is protected from the immune system and from digesting enzymes, e.g., such as proteases, while still remaining completely active. For example, the exemplary SHPNPs can be coated with passivating and targeting ligands without any chemical modification of the payload, e.g., the enzyme load, providing an effective strategy for in vivo applications.

Figure 16:
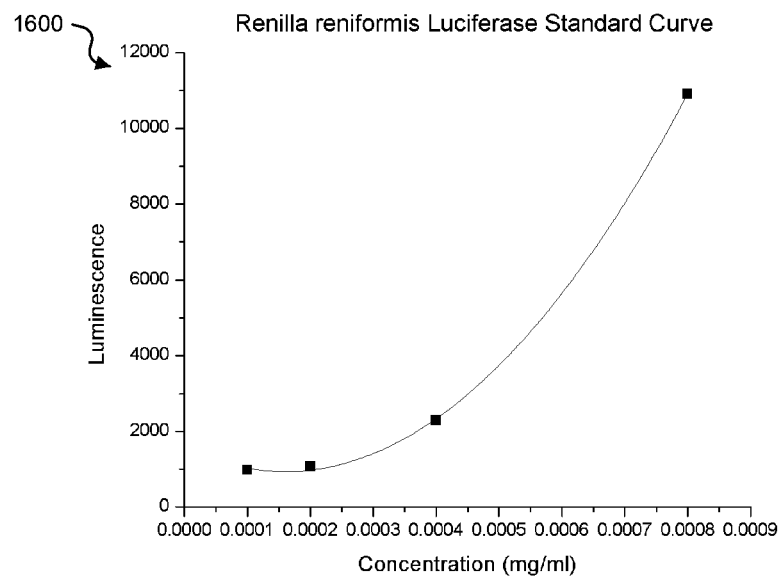
FIG. 16 shows a data plot showing a standard curve of *Renilla reniformis* luciferase activity.
Figure 17:
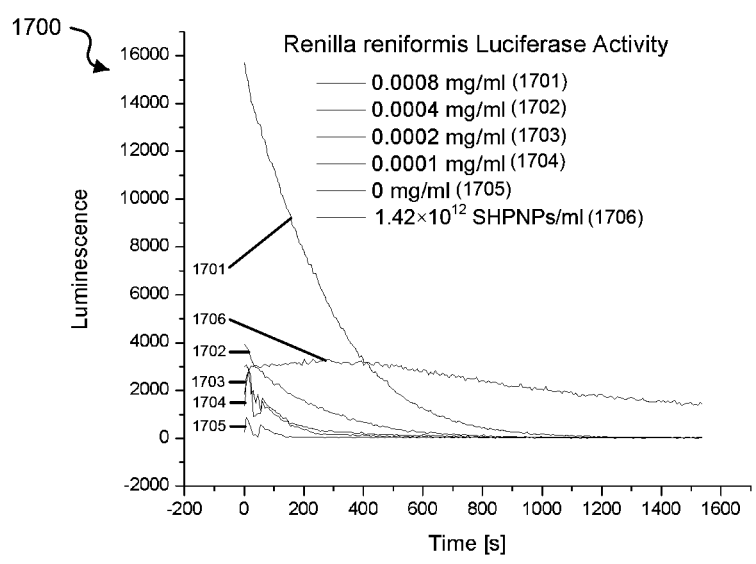
FIG. 17 shows a data plot showing activity of different concentrations of *Renilla reniformis* luciferase compared to that encapsulated within sealed hollow porous nanoparticles.

Exemplary implementations were performed to characterize the enzymatic activity and protection abilities of the disclosed SHPNPs. For example, penicillinase from *Bacillus cereus* is a member of the family of beta-lactamases which catalyze the hydrolysis of the beta-lactam ring. *B. cereus* penicillinase was utilized in exemplary characterization implementations of SHPNPs, e.g., because it can be considered a preferred beta-lactamase for enzyme-prodrug based therapies, and sensitive chromogenic and fluorogenic assays were available. For example, the latter used the substrate CCF2, which contains a coumarin linked to fluorescein via a cephalosporin group. For example, before cleavage by penicillinase, excitation of the coumarin at 409 nm causes efficient fluorescence resonance energy transfer (FRET) to fluorescein, resulting in green emission peaking around 520 nm. For example, penicillinase cleaves the cephalosporin group, separating fluorescein from coumarin and disrupting FRET, so that the same excitation produces blue 447 nm emission from coumarin. CCF2 is generally available as an acetoxymethyl (AM) ester, which rapidly reverts to CCF2 upon exposure to esterases in rodent plasma and serum as well as inside cells.

FIGS. 10A and 10B are exemplary data plots showing enzymatic activity of sealed hollow porous nanoparticles of the disclosed technology. FIG. 10A shows a data plot 1010 of the activity comparison for SHPNPs with encapsulated penicillinase and CCF2-AM as substrate in normal serum. For example, four exemplary samples were characterized, which included sample 1 of hollow nanoshells, sample 2 of HPNPs, sample 3 of sealed hollow nanoshells, and sample 4 of SHPNPs. All four of the exemplary samples were incubated with enzyme followed by successive washing with 1× PBS and with proteinase-K again after successive washing with lx PBS. The exemplary sealing reaction was performed after enzyme incubation before washing for the exemplary samples 3 and 4. The data shown in the data plot 1010 demonstrates activity of penicillinase enzyme (e.g., MW=28 kDa) encapsulated within the exemplary SHPNPs. All of the exemplary samples were exposed to proteinase-K, e.g., which can digests protein. Therefore, for example, sustained activity of the encapsulated enzyme after exposure to proteinase-K demonstrates the protection of the encapsulated enzyme against proteolysis by encapsulation in SHPNPs (as shown later in FIGS. 12 and 13).

For example, as shown in FIG. 10A, the data plot 1010 shows that the exemplary sample 1 and the exemplary sample 2 demonstrated no or little activity, which was expected after exposure to proteinase-K. For example, the data plot 1010 shows a 2-fold increase in activity of the exemplary sample 3 over the exemplary sample 1, e.g., which can be due to the protection provided by the second layer of silica over the enzymes stuck on the surface supporting the protective effect of the additional silica layer. However, a significant increase in activity was shown by the exemplary sample 4 of the SHPNPs. For example, the data plot 1010 shows a 10-fold activity increase of the SHPNPs over the exemplary sample 3, e.g., demonstrating that the increase is not due to the enzyme covering the surface but rather due to the enzyme molecules filling the hollow interior. The substantial difference shown between the exemplary HPNPs (of sample 2) and the exemplary SHPNPs (of sample 4) further supports this finding, e.g., since these two samples have undergone the same fabrication techniques except for the additional sealing process by the exemplary sample 4.

FIG. 10B shows a data plot 1020 of the activity comparison for polyclonal antibody binding against encapsulated penicillinase. The data plot 1020 includes exemplary red bars 1021 representing the fluorescence from Alexa 488 with streptavidin that can attach antibody molecules with biotin. The data plot 1020 includes exemplary blue bars 1022 representing the fluorescence from Cy5 labeled penicillinase. For example, three exemplary samples were characterized, which included sample 1 of empty SHPNPs, sample 2 of hollow silica shells in which penicillinase was adsorbed on the surface, sample 3 of SHPNPs with encapsulated penicillinase. For example, the exemplary samples 1 and 3 were incubated with proteinase-K to remove any enzyme that might have been stuck to the surface. All three exemplary samples were washed several times to remove unbound enzymes.

The exemplary data plot 1020 shown in FIG. 10B can be used to evaluate the antibody access to the enzyme encapsulated in exemplary SHPNPs. For example, the penicillinase was fluorescently labeled with Cy5, and its accessibility was probed with a rabbit polyclonal biotinylated antibody against penicillinase, e.g., detected by Alexa488-labeled streptavidin. The data plot 1020 shows that the measured intensity from exemplary samples 1 and 3 are comparable (e.g., within the standard error interval), e.g., indicating that the slight fluorescence coming from the exemplary sample 3 is not associated with antibodies, but rather from nonspecific adsorption of Alexa488-streptavidin. For example, the exemplary sample 2 showed around 5-fold higher intensity, e.g., demonstrating significant antibody binding to the enzyme molecules on the surface of the silica. For example, the data plot 1020 shows no fluorescence from the exemplary sample 1, e.g., which was expected due to lack of penicillinase. For example, the data plot 1020 shows no antibody binding to the exemplary sample 3, e.g., although it has the highest amount of penicillinase content, which establishes prevention of antibody access to the encapsulated enzyme within SHPNPs.

FIGS. 10C-10E are electron micrographs showing exemplary nanoparticles. FIG. 10C shows an image 1030 of exemplary 200 nm hollow non-mesoporous nanoshells. FIG. 10D shows an image 1040 of exemplary HPNPs formed by 200 nm templates and 40 nm nanomasks. FIG. 10E shows an image 1050 of exemplary SHPNPs formed by sealing HPNPs (produced by fabrication methods using 200 nm templates and 40 nm nanomasks). Exemplary scale bars represent 100 nm in the images 1030, 1040, and 1050.

FIG. 11 shows an image 1100 demonstrating in vivo activity in BALB/c mice of *Renilla reniformis* luciferase (RenLuc) enzyme. For example, the exemplary RenLuc enzyme was encapsulated in 200 nm SHPNPs in a similar manner as penicillinase was in the previous implementation, e.g., including shaving with proteinase-K to remove any surface-exposed RenLuc. The illuminated and luminescence pictures in the image 1100 were overlaid. For example, an exemplary BALB/c mouse 1101 (shown on the left of the image 1100) was injected intramuscularly with 100 μL of RenLuc enzyme encapsulated SHPNP solution at a concentration of $5.68\times10^{12}$ particles/mL, followed by lateral tail vein injection of 10 μg benzyl-coelenterazine after 5 minutes. As a control, an exemplary mouse 1102 (shown on the right of the image 1100) was injected intramuscularly with 100 μL of 8 μg/mK concentration of free RenLuc enzyme. Both exemplary injections demonstrated similar in vitro activity (as shown later in FIGS. 16 and 17). For example, the data obtained in the image 1100 included an exemplary procedure in which 5 min after intramuscular injection, 10 μg benzyl-coelenterazine was administered intravenously in the lateral tail vein. Luminescence intensities were measured from each mouse 5 minutes after intravenous injections. Luminescence intensity from the mouse injected with RenLuc encapsulated SHPNPs was measured as $2.6 \times 10^5$ p/sec/cm²/sr indicating localized activity of encapsulated enzymes within SHPNPs, whereas the intensity from the mouse injected with free RenLuc was below the detectable limit. For example, lack of luminescence from the latter may be mainly due to diffusion of free enzyme out of the injection site.

Figure 12:
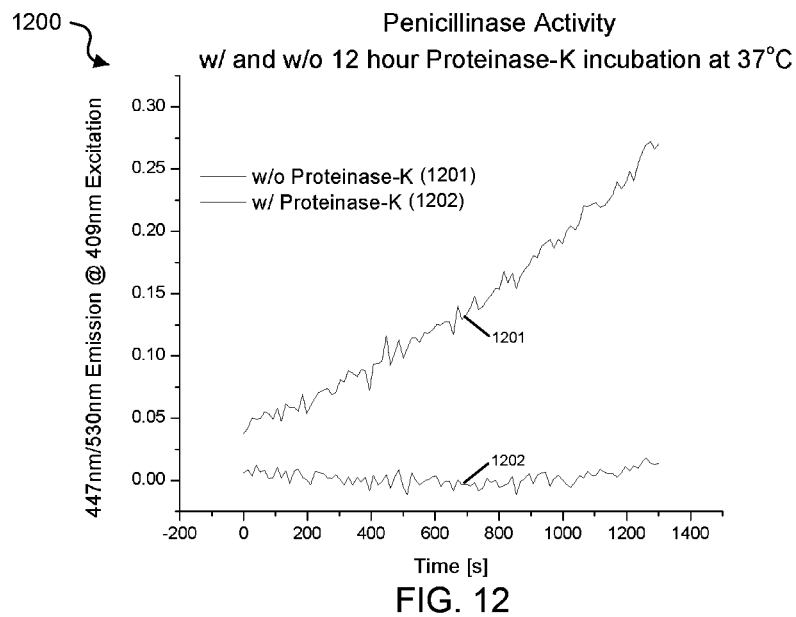
FIG. 12 shows a data plot showing activity of free *Bacillus cereus* penicillinase with and without incubation with proteinase-K.

FIG. 12 shows a data plot 1200 showing activity plots of free *Bacillus cereus* penicillinase with and without incubation with proteinase-K for 12 hours at 37° C. in 1× normal mouse serum. For example, 5 μM CCF2-AM was used as substrate, and the activity was measured in 100% normal mouse serum as the initial rate of increase of the ratio of blue fluorescence (447 nm) to green fluorescence (520 nm) with excitation at 409 nm. The data plot 1200 includes a plotted data 1201 of free *Bacillus cereus* penicillinase without incubation with proteinase-K and a plotted data 1202 of free *Bacillus cereus* penicillinase with incubation with proteinase-K.

Figure 13:
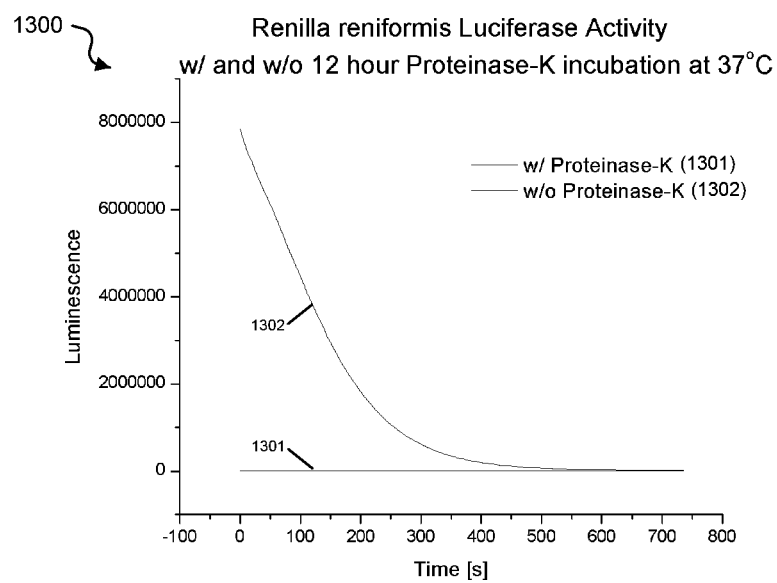
FIG. 13 shows a data plot showing activity of free *Renilla reniformis* luciferase with and without incubation with proteinase-K.

FIG. 13 shows a data plot 1300 showing activity plots of free *Renilla reniformis* luciferase with and without incubation with proteinase-K for 12 hours at 37° C. in 1× normal mouse serum. For example, each reaction was 100 μL in total containing 10 μg/mL benzyl-coelenterazine as substrate. The data plot 1300 includes a plotted data 1301 of free *Renilla reniformis* luciferase with incubation with proteinase-K and a plotted data 1302 of free *Renilla reniformis* luciferase without incubation with proteinase-K.

Figure 14:
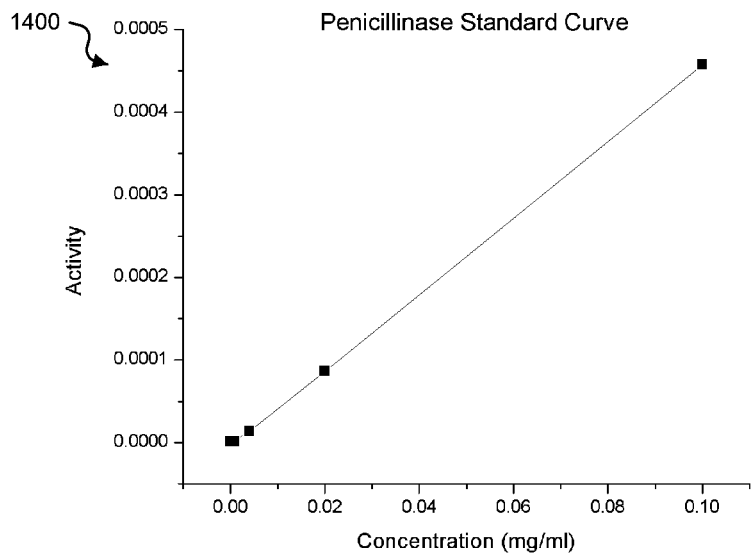
FIG. 14 shows a data plot showing a standard curve of *Bacillus cereus* penicillinase activity.

FIG. 14 shows a data plot 1400 showing a standard curve of *Bacillus cereus* penicillinase activity. For example, initial rate of increase in absorbance in nitrocefin assay was represents the vertical axis of the data plot 1400.

Figure 15:
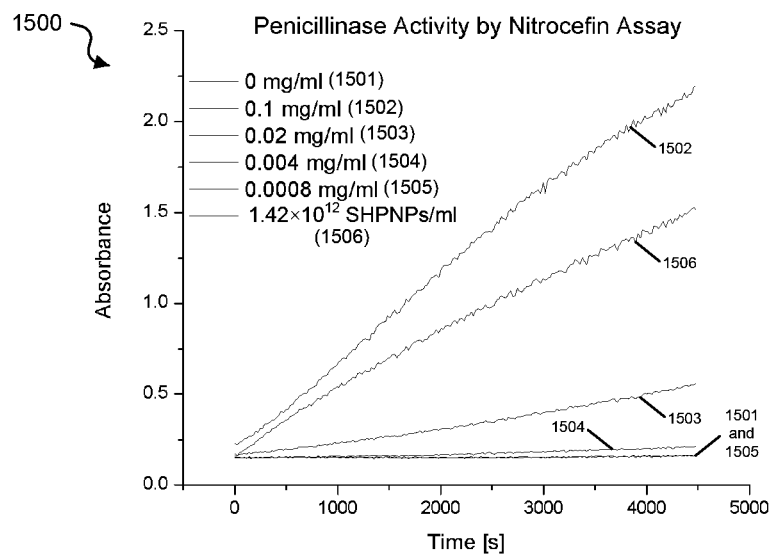
FIG. 15 shows a data plot showing activity of different concentrations of free *Bacillus cereus* penicillinase compared to that encapsulated within sealed hollow porous nanoparticles.
Figure 18A:
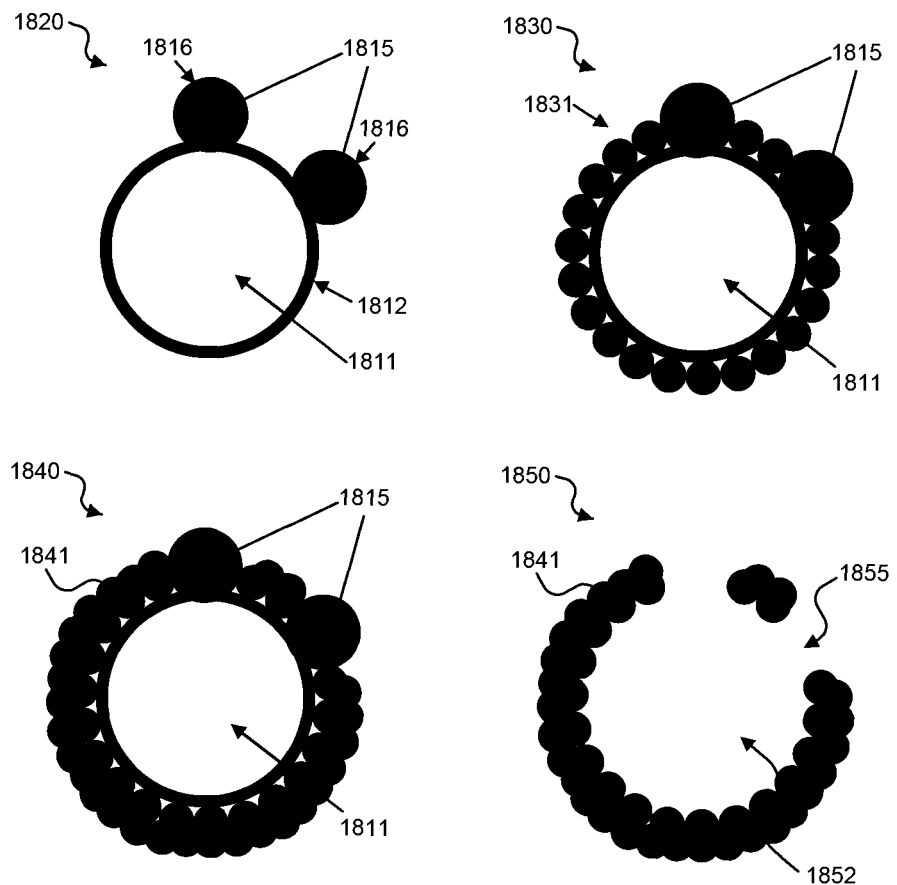
FIGS. 18A and 18B show schematic diagrams illustrating an exemplary metallic nanoparticle synthesis protocol.

FIG. 15 shows a data plot 1500 showing activity plots of different concentrations of free *Bacillus cereus* penicillinase compared to *B. cereus* penicillinase encapsulated within sealed hollow porous nanoparticles with a concentration of $1.42 \times 10^{12}$ particles/mL. For example, each reaction was 100 μL in total containing 250 μg/mL nitrocefin as substrate, and absorbance was measured at 486 nm. For example, the data plot 1500 shows penicillinase activity for concentrations including 0 mg/mL (curve 1501), 0.1 mg/mL (curve 1502), 0.02 mg/mL (curve 1503), 0.004 mg/mL (curve 1504), and 0.0008 mg/mL (curve 1505), and shows $1.42\times10^{12}$ SHPNPs/mL (curve 1506).

For example, the standard curve of free *B. cereus* penicillinase (shown in the data plot 1400) compared to the measured activity of the *B. cereus* penicillinase encapsulated within the SHPNPs corresponded to $4.58\times10^{-14}$ international units (IU) from a single 200 nm SHPNP, e.g., ~50 enzyme molecules per particle based on a yield of HPNP synthesis is 100%. For example, during enzyme loading, HPNPs were initially incubated with 26.4 μM. For example, the assayed concentration of enzyme within a single SHPNP can correspond to 19.5 μM, e.g., resulting in 74% apparent loading efficiency. Exemplary factors that may affect this percentage include the following. For example, the yield of HPNP synthesis may be less than 100% resulting in broken HPNPs that cannot be sealed but are still counted as SHPNPs. For example, there may be some enzyme leakage out of the particle during the dilution for silica polycondensation reaction. For example, the access of substrate to enzyme may be limited by diffusion of substrate through the porous shell. For example, the enzyme concentration within particles can be adjustable by the concentration of the enzyme solution during the sealing reaction.

FIG. 16 shows a data plot 1600 showing a standard curve of *Renilla reniformis* luciferase activity. Luminescence intensity produced as a result of interaction with benzyl-coelenterazine represents the vertical axis of the data plot 1600.

FIG. 17 shows a data plot 1700 showing activity plots of different concentrations of *Renilla reniformis* luciferase compared to *R. reniformis* luciferase encapsulated within sealed hollow porous nanoparticles with a concentration of $1.42\times10^{12}$ particles/mL. For example, each reaction was 100 μL in total containing 10 ng/mL benzyl-coelenterazine as substrate. The data plot 1700 shows *Renilla reniformis* luciferase activity for concentrations including 0.0008 mg/mL (curve 1701), 0.0004 mg/mL (curve 1702), 0.0002 mg/mL (curve 1703), 0.0001 mg/mL (curve 1704), and 0 mg/mL (curve 1705), and shows $1.42\times10^{12}$ SHPNPs/mL (curve 1706).

The disclosed SHPNPs demonstrate a platform for encapsulating functional biomolecules, e.g., such as enzymes, acting on small molecule substrates that can freely diffuse in and out through the SHPNPs' small size pores. The disclosed SHPNPs can be manufactured in large quantities with sizes and characteristics that can be tightly controlled and the enzyme can be kept in a controlled environment protected from any specific or nonspecific interference from other biomolecules. Exemplary implementations of the disclosed SHPNPs demonstrated that encapsulated enzymes maintain their activities and are effectively shielded from antibodies or proteases, e.g., since the pores of the shells are smaller than the antibodies, proteases, or such molecules. Moreover, for example, surface modifications of SHPNPs can enhance circulation and targeting in vivo, e.g., without the need of any modification on the encapsulated payload. The disclosed technology provides flexible fabrication techniques of the described SHPNPs with control of particle dimensions and permeability, and the disclosed SHPNPs can be tailored and optimized for specific loads and substrates.

In another aspect, the disclosed technology can include fabrication protocols for fabricating the metallic nanoparticles with hollow core, porous surface and sealable holes. FIGS. 18A and 18B show schematic diagrams illustrating one exemplary metallic nanoparticle synthesis protocol.

FIG. 18A shows a process 1820 of binding masking particles 1815 having a functionalized surface 1816 (e.g., a carboxylated surface) to a functionalized surface 1812 (e.g., an aminated surface) of a template core particle 1811, e.g., by electrostatic attraction. For example, since the exemplary carboxylated particles 1815 have a negatively charged surface, they repel negative ions and prevent sol-gel reaction on their surface, e.g., blocking some positively charged regions of the outer surface of the exemplary aminated template particle 1811.

FIG. 18A shows a process 1830 of adding a colloidal metallic layer 1831 (e.g., colloidal gold) to the masking particles 1815-template core particle 1811 complex. For example, sol-gel reagents can be added to the solutions containing the masking particles bound to the template particles. The exemplary sol-gel reactions can occur in the positively charged regions along the surface 1812 of the template core particle 1811, e.g., the regions that are not covered or blocked by the masking particles 1815, forming the exemplary colloidal gold layer 1831.

FIG. 18A shows a process 1840 of thickening the initial layer 1831 into a thick layer 1841. For example, the initial layer 1831 can be formed from colloidal gold generated through sol-gel reactions in the process 1830. The exemplary colloidal gold layer 1831 can act as a nucleation site for further growth of gold, e.g., forming the thick layer 1841. For example, the process 1840 can include the addition of auric acid and formaldehyde as reducing agent for the formation of the exemplary thick gold layer 1841.

FIG. 18A shows a process 1850 showing forming a hollow porous nanoparticle, e.g., by removing the template particle 1811 and the masking particles 1815. For example, once the layer 1841 is formed with the desired thickness, the template and masking particles are removed, e.g., by various methods including dissolving them by solvents, calcination, melting, or burning, or a combination of these or other similar methods. For example, implementation of the process 1850 yields a metallic HPNP (e.g., a gold HPNP) that includes empty or hollowed porous shell 1841 with holes 1855 and an empty or hollowed interior 1852.

Figure 18B:
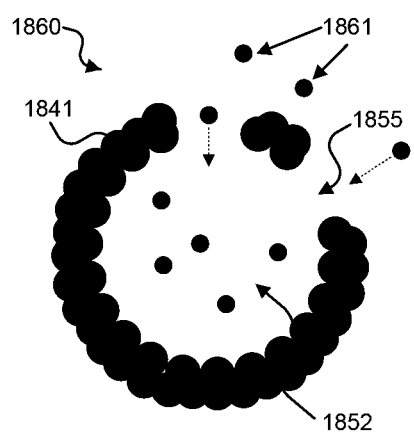
Figure 18C:
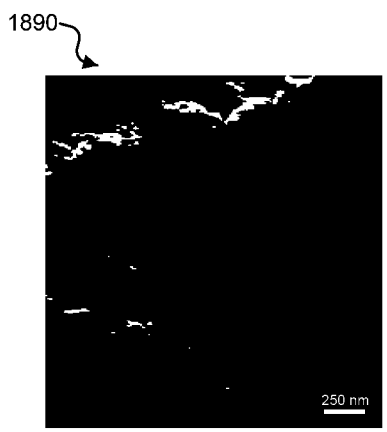
FIG. 18C shows an image of exemplary hollow porous gold nanoparticles.

Once the exemplary metallic HPNPs are created, they can be loaded with other substances and sealed to encapsulate the other substances, e.g., by implementing methods previously described and illustrated in FIGS. 1B and 1C. For example, FIG. 18B shows a process 1860 of loading load particles 1861 into the hollow interior region 1852 of the metallic HPNP 1841. For example, a solution of metallic HPNPs can be loaded with the load substances by adding a high concentration solution of the load substances to the solution of the metallic HPNPs. The process 1860 can be implemented by one of several methods. In one example, the load particles 1861 can diffuse into the metallic HPNPs 1841 through the holes 1855. In other examples, the load particles 1861 can enter the interior region 1852 of the metallic HPNPs 1841 through their holes 1855 by non-diffusion means, e.g., including electrophoretic forces. The process 1860 can be implemented using various types of materials as the load, e.g., including, but not limited to, drugs, biodegradable macromolecules, pH sensitive molecules, enzymes and/or other proteins, lipids, metals, polymers, and ceramic particles, for various applications. For example, subsequent to implementation of the process 1860, the metallic HPNPs 1841 can be sealed to form sealed metallic HPNPs (metallic SHPNPs), e.g., by implementing the process 170 previously described and shown in the FIG. 1C. FIG. 18C shows an image 1890 showing after an exemplary gold HPNP before 500 nm aliphatic-amine polystyrene core extraction.

Figure 19:
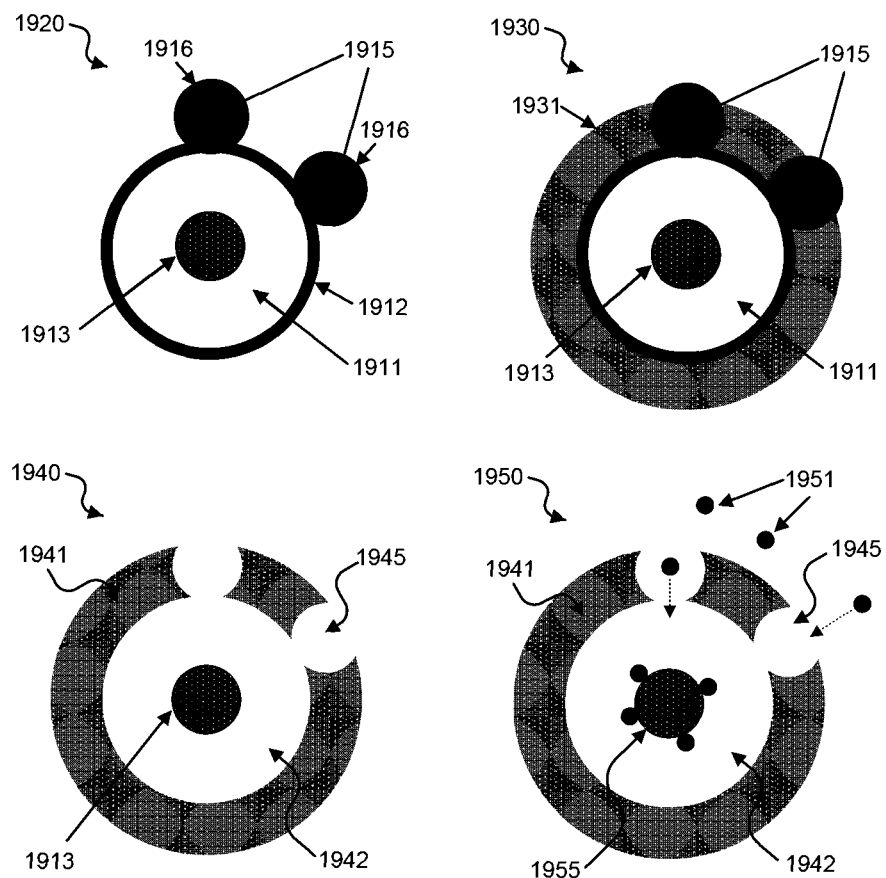
FIG. 19 shows schematic diagrams illustrating an exemplary nanoparticle synthesis protocol.

In another aspect, the disclosed technology can include fabrication protocols for fabricating the nanoparticles having one or more interior particles within a hollow core, porous surface and sealable holes. FIG. 19 shows schematic diagrams illustrating one exemplary nanoparticle synthesis protocol.

FIG. 19 shows a process 1920 of binding masking particles 1915 having a functionalized surface 1916 (e.g., a carboxylated surface) to a functionalized surface 1912 (e.g., an aminated surface) of a template core particle 1911, the template particle 1911 having at least one interior particle 1913. For example, the template particle 1911 can be an outer coating of the at least one interior particle 1913 or the template particle 1911 can be a hollow particle that encloses the least one interior particle 1913 within its hollow interior. For example, the process 1920 can include binding the masking particles 1915 to the surface 1912 of the template particle 1911 by electrostatic interactions or means, e.g., including, but not limited to, hydrogen bonding, covalent bonding, magnetic attraction, hydrophobic interactions, etc. For example, since the exemplary carboxylated particles 1915 have a negatively charged surface, they repel negative ions and prevent sol-gel reaction on their surface, e.g., blocking some positively charged regions of the outer surface of the exemplary aminated template particle 1911.

FIG. 19 shows a process 1930 of adding a layer 1931 (e.g., silica) to the masking particles 1915-template core particle 1911 complex. For example, sol-gel reagents can be added to the solutions containing the masking particles bound to the template particles. The exemplary sol-gel reactions can occur in the positively charged regions along the surface 1912 of the template core particle 1911, e.g., the regions that are not covered or blocked by the masking particles 1915, forming the exemplary layer 1931.

FIG. 19 shows a process 1940 of forming a hollow porous nanoparticle including the interior particle 1913 within an interior region 1942, e.g., by removing the template particle 1911 and the masking particles 1915. For example, once the layer 1931 is formed with the desired thickness, the template and masking particles are removed, e.g., by various methods including dissolving them by solvents, calcination, melting, or burning, or a combination of these or other similar methods. For example, implementation of the process 1940 yields an HPNP that includes a porous shell 1941 that includes the interior particle 1913 within its hollowed interior region 1942 and holes 1945 distributed throughout the porous shell 1941, e.g., based on the initial location of the bound masking particles 1915 to the template particle 1911.

Once the exemplary HPNPs including the at least one interior particle are created, they can be loaded with other substances and sealed to encapsulate the other substances, e.g., by implementing methods previously described and illustrated in FIGS. 1B and 1C. For example, FIG. 19 shows a process 1950 of loading load particles 1951 into the hollow interior region 1942 of the HPNP 1941. For example, a solution of the exemplary HPNPs including the enclosed interior particle(s) can be loaded with the load substances by adding a high concentration solution of the load substances to the solution of the exemplary HPNPs. The process 1950 can be implemented by one of several methods. In one example, the load particles 1951 can diffuse into the HPNPs 1941 through the holes 1945. In other examples, the load particles 1951 can enter the interior region 1942 of the HPNPs 1941 through their holes 1945 by non-diffusion means, e.g., including electrophoretic forces. The process 1950 can be implemented using various types of materials as the load, e.g., including, but not limited to, drugs, biodegradable macromolecules, pH sensitive molecules, enzymes and/or other proteins, lipids, metals, polymers, and ceramic particles, for various applications. For example, within the interior region 1942 of the HPNP 1941, the exemplary load particles 1951 can interact with the interior particle 1913, e.g., forming a modified interior particle 1955. For example, the exemplary load particles 1951 can conjugate to the exterior surface of the interior particle 1913, or in other examples, the exemplary load particles 1951 can chemically react with the interior particle 1913. For example, the modified interior particle 1955 may exhibit new properties otherwise not available on the interior particle 1913.

Figure 20:
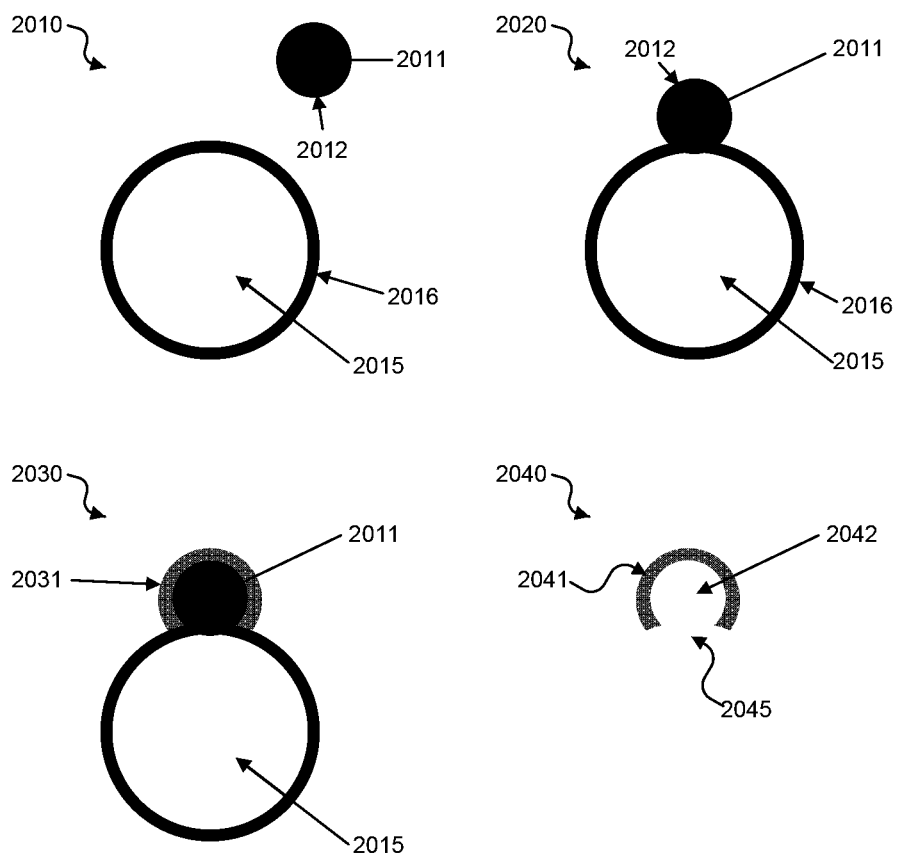
FIG. 20 shows schematic diagrams illustrating an exemplary nanoparticle synthesis protocol.

In another aspect, the disclosed technology can include fabrication protocols for fabricating the nanoparticles having one hole with a hollow core, e.g., in which the hole can be sealable. FIG. 20 show schematic diagrams illustrating one exemplary nanoparticle synthesis protocol.

FIG. 20 shows an example of a process 2010 in which a large masking particle 2015 is mixed together with a core template particles 2011. For example, the large masking particle 2015 can be a nanoparticle configured to have a surface charge, e.g., a negative surface charge. Also, for example, the large masking particle 2015 can include particles with a functionalized external surface 2016, e.g., having a surface charge. For example, the exemplary masking particle 2015 can be a polystyrene nanoparticle, and the exemplary functionalized surface 2016 can be a carboxylated-functional layer. For example, the template particle 2011 can be a nanoparticle configured to have a surface charge, e.g., a positive surface charge, of opposite polarity to the surface charge of the masking particle 2015. Also, for example, the template particle 2011 can include a particle with a functionalized external surface 2012. For example, the exemplary template particle 2011 can be a polystyrene nanoparticle, and the exemplary functionalized surface 2012 can be an amine-functional layer. For example, once the exemplary carboxylated masking particle 2015 and aminated template particle 2011 are mixed, the carboxylated particles 2015 can bind to the aminated template particle 2011.

FIG. 20 also shows an example of a process 2020 of binding of the large masking particle 2015 with the carboxylated functionalized surface 2016 to the aminated functionalized surface 2012 of the template particle 2011, e.g., by electrostatic interactions. In other examples, the process 2020 can include binding the large masking particle 2015 to the surface 2012 of the template particle 2011 by other particle attraction means, e.g., including, but not limited to, hydrogen bonding, covalent bonding, magnetic attraction, hydrophobic interactions, etc.

FIG. 20 further shows an example of a process 2030 of adding a layer 2031 to the template particle 2011. For example, sol-gel reagents can be added to the solutions containing the masking particle 2015 bound to the template particles 2011. Exemplary sol-gel reactions can occur only in the positively charged regions along the surface 2012 of the template particle 2011, e.g., the region that is not covered or blocked by the masking particle 2015. For example, the process 2030 can cover the exposed surface of the template particle 2011 with the coating 2031 while not covering location where the masking particle 2015 is present. For example, the coating 2031 can be a porous material. For example, the layer 2031 can be of a material (e.g., silica) such that the process 2030 can result in a porous layer forming on the surface of the template particle 2011. For example, addition of sol-gel reactants in the process 2030 can initiate silica growth, e.g., rooted from the amino groups of the exemplary aminated functionalized surface 2012. Also for examples, the coating 2031 can be a non-porous material. In some examples, the process 2030 can include adding the layer 2031 to the template particle 2011 by other means, e.g., including, but not limited to, material based exclusivity, or redox chemistry that forms the layer 2031 only on the surface of one particle (e.g., the template particle 2011) and not the surface of the other particle(s) (e.g., the masking particle 2015), among other techniques. Exemplary materials used for the coating can include porous or non-porous materials, or degradable materials (e.g., that can dissolve or degrade in certain environments or under particular conditions or by an exemplary trigger, e.g., conditions and/or trigger including pH, temperature, pressure, molecular interaction, or other conditions and/or triggers).

In addition, FIG. 20 shows an example of a process 2040 of forming a hollow nanoparticle, e.g., by removing the template particle 2011 and the masking particle 2015. For example, once the layer 2031 is formed with the desired thickness, the template particle 2011 and masking particle 2015 are removed, e.g., by various methods including dissolving them by solvents, calcination, melting, or burning, or a combination of these or other similar methods. For example, implementation of the process 2040 yields a hollow nanoparticle that include an empty or hollowed porous shell 2041 with a hole 2045 and a hollowed interior 2042. In some examples, the process 2040 can be implemented to form a hollow nonporous nanoparticle, e.g., when the layer 2031 is of a porous material. In other examples, the process 2040 can be implemented to form a hollow non-porous nanoparticle, e.g., when the layer 2031 is of a non-porous material. Once the exemplary hollow shell structure is formed, it can be loaded with other substances and sealed to encapsulate the other substances, e.g., by implementing methods previously described and illustrated in FIGS. 1B and 1C.

Applications of the described nanoparticle platform can include at least the following. For example, macromolecules larger than the pores can be diffused inside the nanoparticle through holes on the surface and later can be released gradually. For example, once the macromolecules diffuse inside the nanoparticle through holes, holes can be sealed. Since the particle surface is porous, small molecules can diffuse in and outside therefore providing communication of the macromolecule with the outside environment while protecting either the environment from macromolecules or protecting the macromolecules from environment. For example, macromolecule inside the particle can be used as a sensor reporting some event in the environment without being exposed to the environment. For example, once the macromolecules diffused inside the particle, the holes can be sealed with molecules having a particular property (e.g., such as a degradation property). For example, the particular property can be exploited, and the macromolecules encapsulated in the particle can be released. For example, the macromolecules sealed inside the HPNP can include a particular property such as reacting with a molecule small enough to pass through the pores. For example, the macromolecule might be an enzyme molecule used to activate a small drug molecule. Since the exemplary enzyme molecule is encapsulated inside the particle, it is hidden from the immune system. For example, the surface of HPNPs can be functionalized with targeting agents, e.g., for efficient deployment and delivery to the target region. For example, an inactivated drug can be introduced to the circulation separately. Since the exemplary drug is not activated, the drug is not dose limited. For example, once the exemplary inactivated drug and enzyme-loaded HPNP meet in the target region of the body, the drug can diffuse inside the HPNP and become activated by the enzyme; and the activated drug can diffuse out of the HPNP to the target region, e.g., thereby affecting only the target region.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few implementations and examples are described and other implementations, enhancements and variations can be made based on what is described and illustrated in this patent document.

What is claimed is:

1. A nanoparticle for carrying a payload substance, comprising:
    a shell structure including at least two layers including an internal layer and an external layer;
    wherein the internal layer encloses a hollow interior region comprising a payload substance in the hollow interior region;
    wherein the internal layer includes one or more holes penetrating said internal layer;
    wherein the external layer is attached to the internal layer and formed around the internal layer;
    wherein the payload substance is capable of passing through the one or more holes of the internal layer;
    and wherein the payload substance is incapable of passing through the external layer.

2. The nanoparticle of claim 1, wherein the shell structure comprises a material that includes at least one of silica, gold, or calcium phosphate.

3. The nanoparticle of claim 1, wherein the payload substance is selected from the group consisting of a drug, a biodegradable molecule, a pH sensitive molecule, an enzyme, a protein, a hormone, a glycoprotein, a glycolipid, a nucleic acid, an aptamer, a lipid, and combinations thereof.

4. The nanoparticle of claim 1, further comprising a ligand molecule conjugated to the shell structure, the ligand molecule having an affinity to a receptor molecule found on a target structure to attract and bind the shell structure to the target structure.

5. The nanoparticle of claim 4, wherein the target structure is a living tissue within an organism, and the shell structure is capable of binding to the living tissue.

6. The nanoparticle of claim 5, wherein the living tissue is a tumor.

7. The nanoparticle of claim 5, wherein the shell structure protects the substance from an immune response.

8. The nanoparticle of claim 5, wherein the external layer is porous.

9. The nanoparticle of claim 8, wherein the shell structure of the nanoparticle allows an inactivated molecule to enter the hollow interior region of the nanoparticle by passing through pores of the external layer and the holes of the internal layer.

10. The nanoparticle of claim 9, wherein the inactivated molecule that has entered the hollow interior region is capable of interacting with the payload substance to form an activated molecule, and wherein the shell structure allows the activated molecule to exit the hollow interior region of the nanoparticle by passing through the holes of the internal layer and the pores of the external layer.

11. The nanoparticle of claim 10, wherein the payload substance is an enzyme and the wherein the inactivated molecule is a substrate capable of interacting with said enzyme.

12. The nanoparticle of claim 10, wherein the payload substance is an enzyme and the inactivated molecule is a prodrug, wherein the prodrug and the enzyme are capable of interacting to form an active drug.

13. The nanoparticle of claim 10, wherein the payload substance is a macromolecule sensitive to changes in pH and the inactivated molecule is an ion.

14. The nanoparticle of claim 8, wherein, when the nanoparticle is deployed into an environment having waste molecules, the shell structure of the nanoparticle allows the waste molecules to enter the hollow interior region of the shell structure through the plurality of pores in the external and holes in the internal layer in order to interact with the payload substance.

15. The nanoparticle of claim 14, wherein the waste molecules, when present in the hollow interior region, are capable of binding to the payload substance.

16. The nanoparticle of claim 1, wherein the holes of the internal layer are mesopores sized from 2-50 nm.

17. The nanoparticle of claim 8, wherein the pores of the porous external layer are nanopores sized less than 2 nm in diameter.

18. The nanoparticle of claim 8, wherein the holes of the internal layer are mesopores sized from 2-50 nm and the pores of the porous external layer are nanopores sized less than 2 nm in diameter.

* * * * *